(12) United States Patent
Bauer et al.

(10) Patent No.: US 7,915,240 B2
(45) Date of Patent: Mar. 29, 2011

(54) IMMUNOMODULATORY COMPOUNDS AND TREATMENT OF DISEASES RELATED TO AN OVERPRODUCTION OF INFLAMMATORY CYTOKINES

(75) Inventors: Jacques Bauer, Saint-Pres (CH); Carlo Chiavaroli, Thoiry (FR); Stéphane Moutel, Bonne (FR)

(73) Assignee: OM Pharma, Meyrin (CH)

( * ) Notice: Subject to any disclaimer, the term of this patent is extended or adjusted under 35 U.S.C. 154(b) by 0 days.

(21) Appl. No.: 12/279,845

(22) PCT Filed: Mar. 9, 2007

(86) PCT No.: PCT/IB2007/000567
§ 371 (c)(1),
(2), (4) Date: Sep. 29, 2008

(87) PCT Pub. No.: WO2007/102081
PCT Pub. Date: Sep. 13, 2007

(65) Prior Publication Data
US 2009/0054378 A1 Feb. 26, 2009

(30) Foreign Application Priority Data

Mar. 9, 2006 (WO) .................. PCT/IB2006/050748

(51) Int. Cl.
*A01N 57/00* (2006.01)
*A61K 31/66* (2006.01)
(52) U.S. Cl. ...................................................... 514/119
(58) Field of Classification Search ........................ None
See application file for complete search history.

(56) References Cited

U.S. PATENT DOCUMENTS

| | | | |
|---|---|---|---|
| 6,297,257 B1 * | 10/2001 | Napoletano et al. .......... | 514/307 |
| 6,831,069 B2 | 12/2004 | Tam et al. | |
| 7,157,092 B1 * | 1/2007 | Bauer et al. ................ | 424/278.1 |
| 7,799,762 B2 * | 9/2010 | Bauer et al. ................ | 424/278.1 |
| 2003/0203852 A1 * | 10/2003 | Bauer et al. ...................... | 514/19 |
| 2005/0192232 A1 * | 9/2005 | Bauer et al. ...................... | 514/19 |
| 2006/0148678 A1 * | 7/2006 | Bauer et al. ........................ | 514/7 |

FOREIGN PATENT DOCUMENTS

| | | | |
|---|---|---|---|
| DE | 20220947 | * | 2/2002 |
| EP | 1 081 132 A1 | * | 5/1999 |
| EP | 1 081 132 A1 | | 3/2004 |
| EP | 2051728 | | 4/2009 |
| WO | WO00/00462 | * | 12/2000 |
| WO | WO 01/46127 | * | 6/2001 |
| WO | WO 01/57233 | | 8/2001 |
| WO | WO 01/57233 A2 | * | 8/2001 |

OTHER PUBLICATIONS

Frieri. Nitric Oxide in Allergic Rhinitis and Asthma. Allergy and Asthma Proceedings. 1998, No. 19, pp. 349-351.*
Chan et al. Nitric oxide and vascular responses in Type I diabetes. Diabetologia. 2000. vol. 43, pp. 137-147.*
Taniuchi et al. Increased serum nitrate levels in infants with atopic dermatitis. Allergy, 2001. vol. 56, pp. 693-695.*
EPO machine language translation from German to English for DE 20220947, Feb. 2002, 29 pages.*
Byl et al., "OM197-MP-AC induces the maturation of human dendritic cells and promotes a primary T cell responce," Int. Immunopharm., vol. 3, pp. 417-425 (2003).
European Communication Pursuant to Article 94(3) EPC, Apr. 12, 2010, for OM Pharma, European Application No. 07733936.4, filed Mar. 9, 2007.

\* cited by examiner

*Primary Examiner* — Marcela M Cordero Garcia
(74) *Attorney, Agent, or Firm* — Law Offices of Albert Wai-Kit Chen, PLLC

(57) ABSTRACT

Method of using immunomodulatory compounds for treating diseases related to an overproduction of inflammatory cytokines, including diseases selected from asthma, atopic dermatitis, allergic rhinitis, prostatitis, inflammatory bowel disease, diabetes, and rhumatoid arthritis, the compounds being of general formula (I):

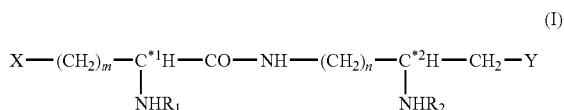

(I)

wherein:
m and n, independently from each other, are an integer ranging from 1 to 4,
X and Y represent —COOH, —O—P(O)(OH)$_2$, —O—SO$_2$(OH), —NH$_2$, —OH, —CONH(CH$_2$)$_{n1}$—NH$_2$, —CO—NH—CH(COOH)—(CH$_2$)$_{n1}$—COOH, —CO—NH—CH(COOH)—(CH$_2$)$_{n1}$—NH$_2$, —O—CO—(CH$_2$)$_{n1}$—NH$_2$, —O—CO—(CH$_2$)$_{n1}$—CHOH—CH$_2$OH, —O—CO—(CH$_2$)$_{n1}$—OH, —O—CO—(CH$_2$)$_{n1}$—COOH, —O—CO—(CH$_2$)$_{n1}$—CHO, —O—CO—(CH$_2$)$_{n1}$—NH—CO—(CH$_2$)$_{n2}$—COOH,
R$_1$ and R$_2$ each designate an acyl group derived from a saturated or unsaturated, straight- or branched-chain carboxylic acid having from 2 to 18 carbon atoms, which is unsubstituted or bears one to three substituents selected among hydroxyl, dihydroxyphosphoryloxy, alkyl of 2 to 18 carbon atoms, alkoxy of 2 to 18 carbon atoms, acyloxy of 2 to 18 carbon atoms in the acyl moiety, amino, acylamino.

13 Claims, 16 Drawing Sheets

Figure 3:
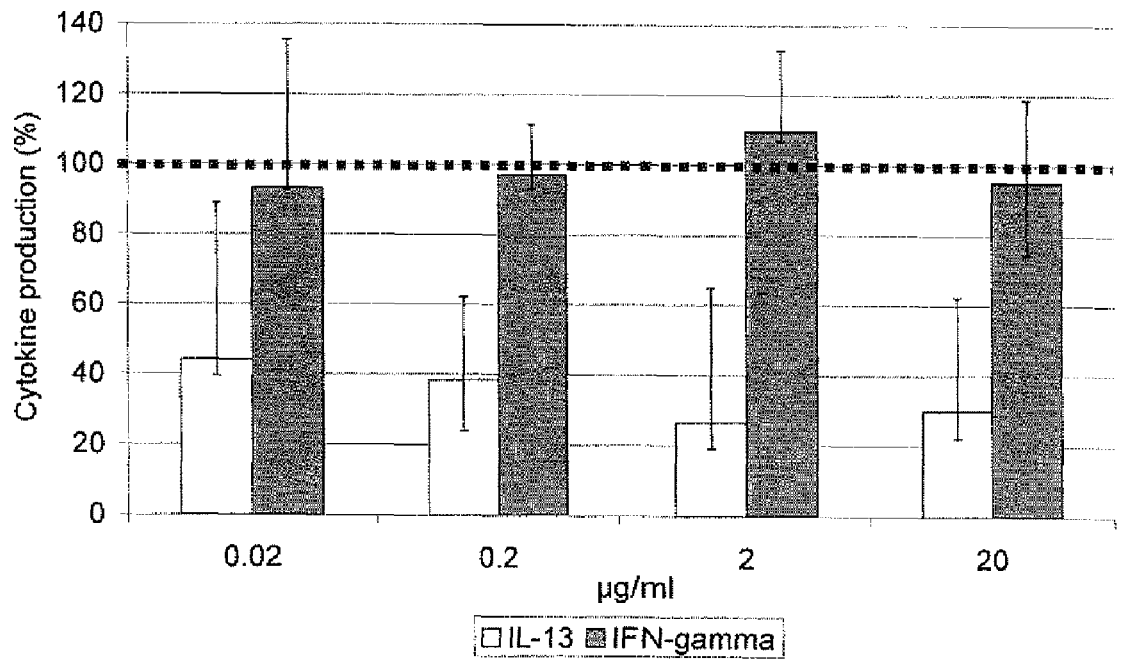
Figure 3:
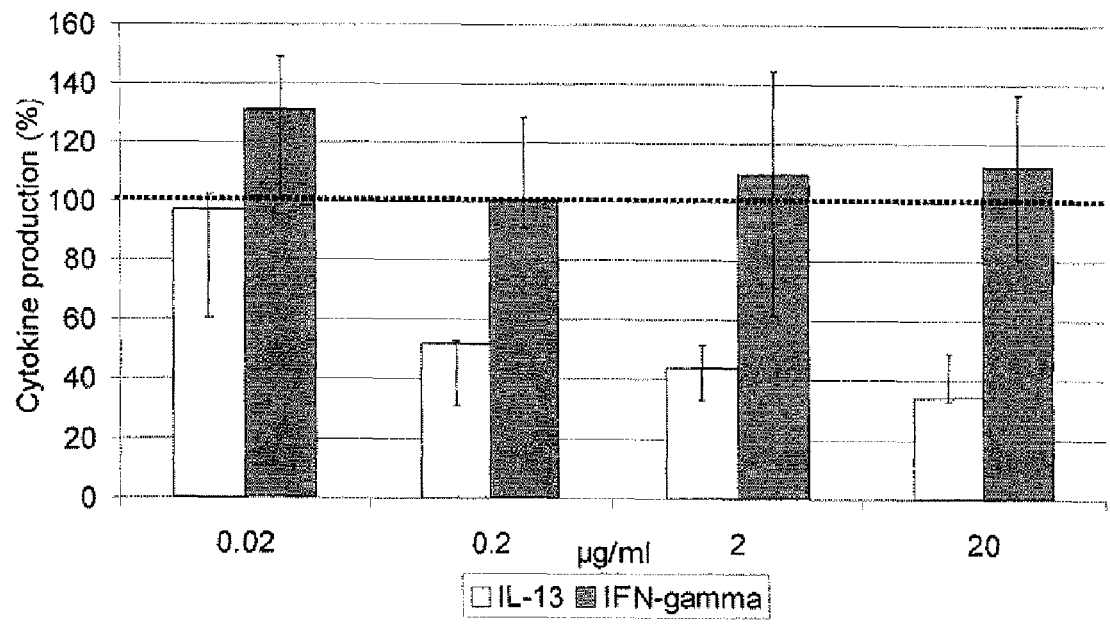

OM-294-BA-MP
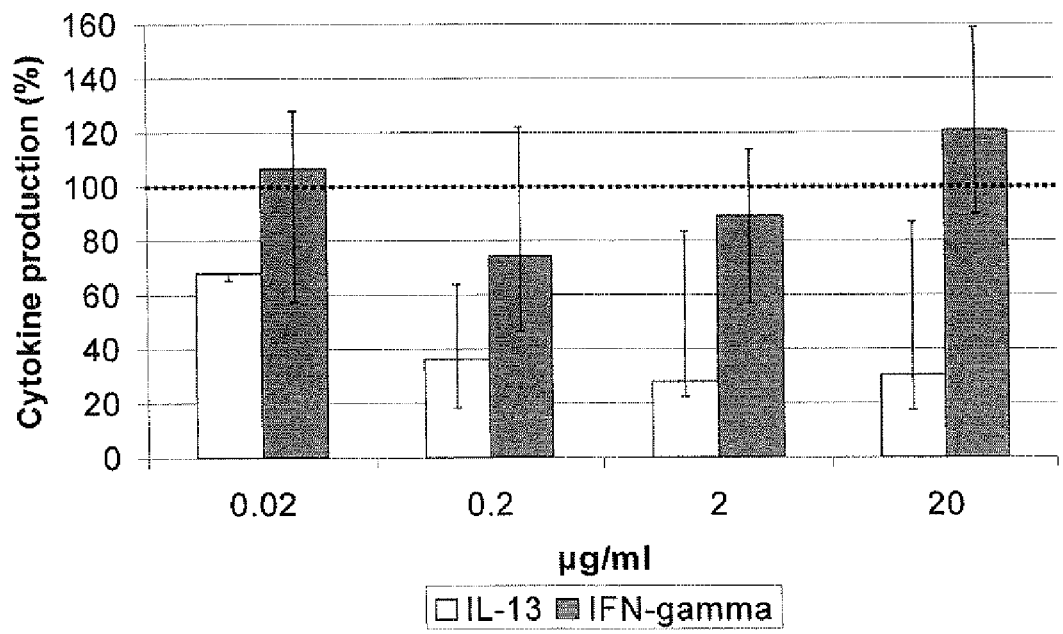
OM-197-MP-HD
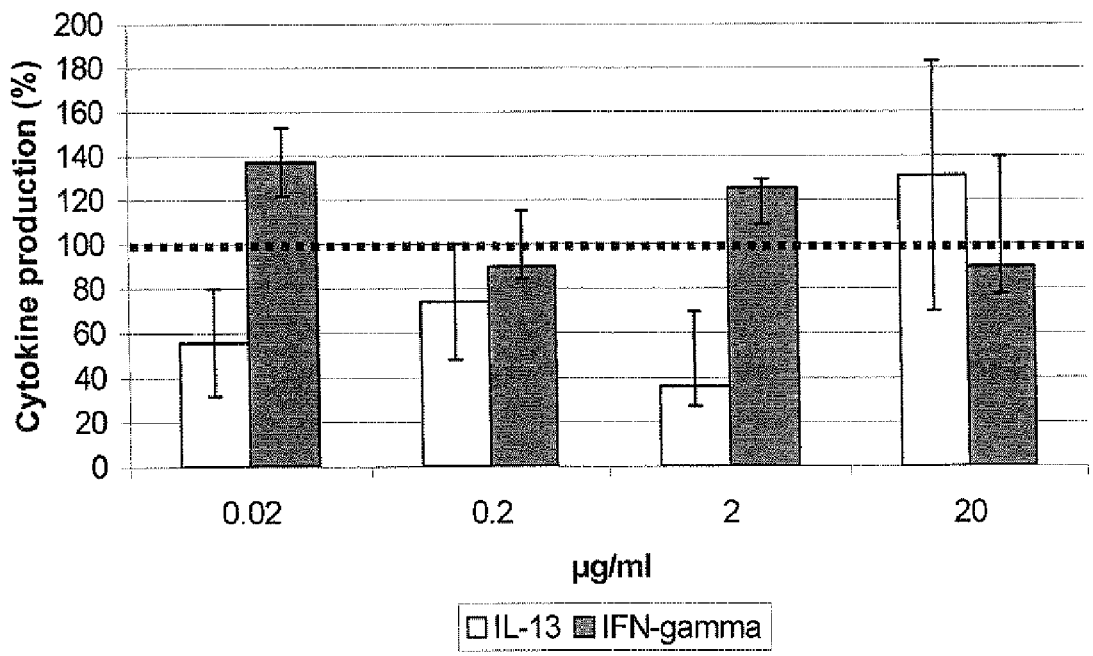
Figure 3 (SUITE)

IMMUNOMODULATORY COMPOUNDS AND TREATMENT OF DISEASES RELATED TO AN OVERPRODUCTION OF INFLAMMATORY CYTOKINES

The invention relates to the use of immunomodulatory compounds for the treatment of diseases related to an overproduction of inflammatory cytokines, such as diseases selected from the group consisting of asthma, atopic dermatitis, allergic rhinitis, prostatitis, inflammatory bowel disease, diabetes, and rhumatoid arthritis.

There have recently been major advances in our understanding of the mechanism of activation of the innate immune system by microbial signals. It has also become clear that such activation of the innate immune system is essential for initiating adaptive immune responses and for determining the type of adaptive responses that are generated. Together these observations have generated a huge renewal of interest in rational approaches to the development of immunotherapy.

Two major discoveries have been crucial to the increased understanding of innate immune activation:
1) the role of dendritic cells (DC) as the antigen-presenting cells responsible for the induction of primary immune responses,
2) the discovery of Toll-like receptors (TLR) and other "pattern recognition" receptors that detect the presence of microbial structures, leading to the stimulation of the innate immune system.

Sallusto and Lanzavecchia first reported that immature DC can be generated from human monocytes in medium supplemented with GM-CSF and IL-4 (Sallusto F, Lanzavecchia A. J Exp Med 1994, 179:1109-18). However, it rapidly became apparent that, in addition to GM-CSF and IL-4, a further maturation factor was required to obtain mature DC that were fully functional as antigen-presenting cells (APC). Mature DC are capable of initiating and steering the adaptive immune response.

Such maturation signals can be provided by microbial products. These products have been show to act through TLRs. Eleven TLRs have been identified, capable or recognising different microbial products. TLR4 is the receptor that specifically recognises bacterial lipopolysaccharide (LPS), one of the most potent stimulators of the innate immune system known.

International application WO 2005 007699 describes the use of specific binding members, in particular of human anti-IL-13 antibody molecules and especially those which neutralise IL-13 activity, in the diagnosis or treatment of IL-13 related disorders, including asthma, atopic dermatitis, allergic rhinitis, fibrosis, inflammatory bowel disease and Hodgkin's lymphoma.

However investigations are still necessary to know the exact role of IL-13 in immunomodulation and the interpretation of the results related to the study of the IL-13/IL-4 pathway are still of hypothetical nature, as shown by the following two recent publications.

The publication "IL-4/IL-13 pathway genetics strongly influence serum IgE levels and childhood asthma" by Michael Kabesch et al., (J. Allergy Clin. Immunol. Volume 117, Number 2) states that IgE production, a hallmark of asthma and atopic disease, may be under genetic control involving genes of the IL-4 and IL-13 pathway. Because IgE switching is fundamental for human immunity and survival, the regulation of IgE is delicate. Although the IL-4/IL-13 pathway may influence the development of asthma mainly through its effect on IgE regulation, the results given indicate that this may not exclusively be the case.

The publication "Control of allergic airway inflammation through immunomodulation" by David B Corry, and Farrah Kheradmand, (J. Allergy Clin. Immunol. Volume 117, Number 2), describes the major findings linked with clinical trials which have changed the management of asthma, and which have not, and that deserve further study. It is reported that IL-4, a cytokine that is required for B-cell IgE responses, is critical to type I hypersensitivity responses, and that IL-4 was therefore one of the first cytokines to be targeted in asthma clinical trials by using a soluble form of the IL-4 receptor α chain (sIL-4Rα), which binds to and inactivates IL-4. IL-13 is another cytokine that has many of the same effects as IL-4 but is not inhibited by sIL-4α. The conclusion is that future studies might therefore attempt to inhibit both IL-4 and IL-13 simultaneously for the treatment of asthma.

The present invention relies on the demonstration by the inventors that the molecules as described hereafter are efficient agonists of TLR4 with a good safety profile, that are able to induce the complete maturation of functional monocyte-derived DC, as well activating other cell-types expressing TLR4. DC's treated with compounds according to the invention are able to induce primary T-cell activation and to favour Th1 cellular immune responses.

The inventors also demonstrated that compounds according to the invention are able to markedly decrease the secretion of IL-13 by CD4+ T cells polyclonally-activated by anti-CD3 and anti-CD28 antibodies.

Moreover, when one of the compounds was administered by the i.p. or i.n. routes to a murine model of asthma, the inventors demonstrate a prevention of the allergic responses produced by antigen sensitisation and subsequent aerosol exposure to antigen. The immunological parameters measured suggest a relative decrease in Th2 responses, which may explain the mechanism by which compounds according to the invention are acting in this asthma model. Additionally, the authors demonstrate that the compound of the invention is able to decrease diabetes occurrence in Non Obese Diabetic mice.

The present invention relates to a method for treating warm-blooded animals including humans, suffering from a disease or disorder related to an overproduction of inflammatory cytokines, comprising the administration to a patient in need thereof of an appropriate amount of a pharmaceutical composition comprising at least one immunomodulatory compound of the following general formula (I):

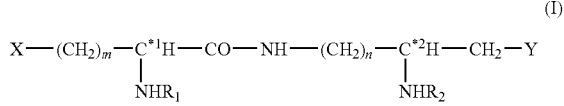

(I)

Wherein
  m and n, independently from each other, are an integer ranging from 1 to 4,
  X and Y each designate a group either in neutral or charged state, selected from the following groups:
    carboxyl —COOH,
    dihydroxyphosphoryloxy —O—P(O)(OH)$_2$,
    hydroxysulfonyloxy —O—SO$_2$(OH),
    amino —NH$_2$,
    hydroxyl —OH,
    [amino(C$_1$-C$_{10}$)alkyl]aminocarbonyl —CONH(CH$_2$)$_{n1}$—NH$_2$, with n$_1$ being an integer from 1 to 10,

[dicarboxy($C_1$-$C_5$)alkyl]aminocarbonyl —CO—NH—CH(COOH)—($CH_2$)$_{n1}$—COOH, with $n_1$ being an integer from 1 to 5, {carboxy[amino($C_1$-$C_5$)alkyl]}aminocarbonyl —CO—NH—CH(COOH)—($CH_2$)$_{n1}$—$NH_2$, with $n_1$ being an integer from 1 to 5, amino($C_1$-$C_{15}$)alkanoyloxy —O—CO—($CH_2$)$_{n1}$—$NH_2$, with $n_1$ being an integer from 1 to 15, dihydroxy($C_1$-$C_{10}$)alkanoyloxy —O—CO—($CH_2$)$_1$—CHOH—$CH_2$OH, with n, being an integer from 1 to 10, hydroxy($C_1$-$C_{10}$)alkanoyloxy —O—CO—($CH_2$)$_{n1}$—OH, with $n_1$ being an integer from 1 to 10, carboxy($C_1$-$C_{10}$)alkanoyloxy —O—CO—($CH_2$)$_{n1}$—COOH, with $n_1$ being an integer from 1 to 10, oxo($C_1$-$C_5$)alkanoyloxy —O—CO—($CH_2$)$_{n1}$—CHO, with $n_1$ being an integer from 1 to 5,

[carboxy($C_1$-$C_{10}$)alkanoyl]amino($C_1$-$C_{15}$)alkanoyloxy —O—CO—($CH_2$)$_{n1}$—NH—CO—($CH_2$)$_{n2}$—COOH, with $n_1$ being an integer from 1 to 10, and $n_2$ being an integer from 1 to 15, $R_1$ and $R_2$ each designate an acyl group derived from a saturated or unsaturated, straight- or branched-chain carboxylic acid having from 2 to 18 carbon atoms, which is unsubstituted or bears one to three substituents selected among hydroxyl, dihydroxyphosphoryloxy, alkyl of 2 to 18 carbon atoms, alkoxy of 2 to 18 carbon atoms, acyloxy of 2 to 18 carbon atoms in the acyl moiety, amino, acylamino, $C^{*1}$ and $C^{*2}$, independently from each other being asymetric carbons in configuration R, S, or in the racemic form RS, or a pharmaceutically acceptable salt, solvate or isomer thereof, optionally in conjugation or admixture with an inert non-toxic pharmaceutically acceptable diluent or carrier.

The invention relates more particularly to a method as defined above, wherein

X is selected from the following groups:
carboxyl —COOH,
dihydroxyphosphoryloxy —O—P(O)(OH)$_2$,
hydroxysulfonyloxy —O—$SO_2$(OH),
amino —$NH_2$,
[amino($C_1$-$C_{10}$)alkyl]aminocarbonyl —CONH($CH_2$)$_{n1}$—$NH_2$, with $n_1$ being an integer from 1 to 10,
[dicarboxy($C_1$-$C_5$)alkyl]aminocarbonyl —CO—NH—CH(COOH)—($CH_2$)$_{n1}$—COOH, with $n_1$ being an integer from 1 to 5,
{carboxy[amino($C_1$-$C_5$)alkyl]}aminocarbonyl —CO—NH—CH(COOH)—($CH_2$)$_{n1}$—$NH_2$, with $n_1$ being an integer from 1 to 5,
amino($C_1$-$C_{15}$)alkanoyloxy —O—CO—($CH_2$)$_{n1}$—$NH_2$, with $n_1$ being an integer from 1 to 15, and Y is selected from the following groups:
dihydroxyphosphoryloxy —O—P(O)(OH)$_2$,
hydroxysulfonyloxy —O—$SO_2$(OH),
amino —$NH_2$,
hydroxyl —OH,
amino($C_1$-$C_{15}$)alkanoyloxy —O—CO—($CH_2$)$_{n1}$—$NH_2$, with $n_1$ being an integer from 1 to 15,
dihydroxy($C_1$-$C_{10}$)alkanoyloxy —O—CO—($CH_2$)$_{n1}$—CHOH—$CH_2$OH, with $n_1$ being an integer from 1 to 10,
hydroxy($C_1$-$C_{10}$)alkanoyloxy —O—CO—($CH_2$)$_{n1}$—OH, with $n_1$ being an integer from 1 to 10,
carboxy($C_1$-$C_{10}$)alkanoyloxy —O—CO($CH_2$)$_{n1}$—COOH, with $n_1$ being an integer from 1 to 10,
oxo($C_1$-$C_5$)alkanoyloxy —O—CO—($CH_2$)$_{n1}$—CHO, with $n_1$ being an integer from 1 to 5,
[carboxy($C_1$-$C_{10}$)alkanoyl]amino($C_1$-$C_{15}$)alkanoyloxy —O—CO—($CH_2$)$_{n1}$—NH—CO—($CH_2$)$_{n2}$—COOH, with $n_1$ being an integer from 1 to 10, and $n_2$ being an integer from 1 to 15.

The invention concerns more particularly a method as defined above, wherein

X is selected from the following groups:
carboxyl —COOH,
dihydroxyphosphoryloxy —O—P(O)(OH)$_2$,
hydroxysulfonyloxy —O—$SO_2$(OH),
amino —$NH_2$,
[amino($C_1$-$C_6$)alkyl]aminocarbony)-CONH($CH_2$)$_{n1}$—$NH_2$, with $n_1$ being an integer from 1 to 6,
[dicarboxy($C_1$-$C_5$)alkyl]aminocarbonyl —CO—NH—CH(COOH)—($CH_2$)$_{n1}$—COOH, with n, being an integer from 1 to 5,
{carboxy[amino($C_1$-$C_5$)alkyl]}aminocarbonyl —CO—NH—CH(COOH)—($CH_2$)$_{n1}$—$NH_2$, with $n_1$ being an integer from 1 to 5,
amino($C_2$-$C_{12}$)alkanoyloxy —O—CO—($CH_2$)$_{n1}$—$NH_2$, with $n_1$ being an integer from 2 to 12, and Y is selected from the following groups:
dihydroxyphosphoryloxy —O—P(O)(OH)$_2$)
hydroxysulfonyloxy —O—$SO_2$(OH),
amino —$NH_2$,
hydroxyl —OH,
amino($C_2$-$C_{12}$)alkanoyloxy —O—CO—($CH_2$)$_{n1}$—$NH_2$, with $n_1$ being an integer from 2 to 12,
dihydroxy($C_3$-$C_7$)alkanoyloxy —O—CO—($CH_2$)$_{n1}$—CHOH—$CH_2$OH, with $n_1$ being an integer from 3 to 7,
hydroxy($C_2$-$C_6$)alkanoyloxy —O—CO—($CH_2$)$_{n1}$—OH, with $n_1$ being an integer from 2 to 6,
carboxy($C_3$-$C_6$)alkanoyloxy —O—CO—($CH_2$)$_{n1}$—COOH, with $n_1$ being an integer from 3 to 6,
oxo($C_2$-$C_5$)alkanoyloxy —O—CO—($CH_2$)$_{n1}$—CHO, with $n_1$ being an integer from 2 to 5,
[carboxy($C_3$-$C_6$)alkanoyl]amino($C_2$-$C_{12}$)alkanoyloxy —O—CO—($CH_2$)$_{n1}$—NH—CO—($CH_2$)$_{n2}$—COOH, with $n_1$ being an integer from 3 to 6, and $n_2$ being an integer from 2 to 12.

The invention relates more particularly to a method as defined above, wherein

X is selected from the following groups:
—COOH,
—O—P(O)(OH)$_2$,
—O—$SO_2$(OH),
—$NH_2$,
—CO—NH—($CH_2$)$_3$—$NH_2$, or —CONH—($CH_2$)$_6$—$NH_2$,
—CO—NH—CH(COOH)—$CH_2$—COOH,
—CO—NH—CH(COOH)—($CH_2$)$_4$—$NH_2$,
—O—CO—($CH_2$)$_5$—$NH_2$, and Y is selected from the following groups:
—O—P(O)(OH)$_2$,
—O—$SO_2$(OH),
—$NH_2$,
—OH,
—O—CO—$CH_2$—$NH_2$ (2-aminoethanoyloxy),
—O—CO—($CH_2$)$_2$—$NH_2$ (3-aminopropanoyloxy),
—O—CO—($CH_2$)$_5$—$NH_2$ (6-aminohexanoyloxy),
or —O—CO—($CH_2$)$_{11}$—$NH_2$ (12-aminododecanoyloxy),
—O—CO—($CH_2$)$_4$—CHOH—$CH_2$OH (6,7-dihydroxyheptanoyloxy), —O—CO—(CH$_2$)$_5$—OH (6-hydroxyhexanoyloxy),
—O—CO—(CH$_2$)$_2$—COOH (3-carboxypropanoyloxy)
—O—CO—(CH$_2$)$_4$—CHO (6-oxohexanoyloxy),
—O—CO—(CH$_2$)$_5$—NH—CO—(CH$_2$)$_2$—COOH (3-carboxypropanoylamino hexanoyloxy).

The invention concerns more particularly a method as defined above, wherein R$_1$ and R$_2$ are chosen among:
—CO—CH$_2$—C*H[O—CO—(CH$_2$)$_{10}$—CH$_3$]—(CH$_2$)$_{10}$—CH$_3$, (3(C$_{12}$O)C$_{14}$),
—CO—CH$_2$—C*HOH—(CH$_2$)$_{10}$—CH$_3$, (3(HO)C$_{14}$),
—CO—CH$_3$, (C2),
—CO—CH$_2$—NH—CO—C*H[O—CO—(CH$_2$)$_8$—CH$_3$]—(CH$_2$)$_5$—CH$_3$, ([2(C$_{10}$O)C$_8$]NC$_2$),
—CO—C*H[O—CO—(CH$_2$)$_4$—CH$_3$]-(CH$_2$)—CH$_3$, (2(C$_6$O)C$_8$),
—CO—(CH$_2$)$_{16}$—CH$_3$, (C18),
—CO—CH$_2$—C*H[O—CH$_2$—C$_6$H$_5$]—(CH$_2$)$_{10}$—CH$_3$, (3(BnO)C$_{14}$),
—CO—CH$_2$—C*H[O—P(O)(OH)$_2$]—(CH$_2$)$_{10}$—CH$_3$, (3[(OH)$_2$—P(O)O]C$_{14}$), C* corresponding to an asymetric carbon in configuration R, S, or in the racemic form RS, in the formulae mentioned above.

The invention relates more particularly to a method as defined above, wherein
R$_1$ is chosen among:
—CO—CH$_2$—C$^{**1}$H[O—CO—(CH$_2$)$_{10}$—CH$_3$]-(CH$_2$)$_{10}$—CH$_3$, (3(C$_{12}$O)C$_{14}$),
—CO—CH$_2$—C$^{**1}$HOH—(CH$_2$)$_{10}$—CH$_3$, (3(HO)C$_{14}$),
—CO—CH$_3$, (C2),
—CO—CH$_2$—NH—CO—C$^{**1}$H[O—CO—(CH$_2$)$_8$—CH$_3$]—(CH$_2$)$_5$—CH$_3$, ([2(C$_{10}$O)C$_8$]NC$_2$),
—CO—C$^{**1}$H[O—CO—(CH$_2$)$_4$—CH$_3$]—(CH$_2$)$_5$—CH$_3$, (2(C$_6$O)C$_8$),
—CO—(CH$_2$)$_{16}$—CH$_3$, (C18),
R$_2$ is chosen among:
—CO—CH$_2$—C$^{**2}$H[O—CO—(CH$_2$)$_{10}$—CH$_3$]—(CH$_2$)$_{10}$—CH$_3$, (3(C$_{12}$O)C$_{14}$),
—CO—CH$_2$—C$^{**2}$HOH—(CH$_2$)$_{10}$—CH$_3$, (3(HO)C$_{14}$),
—CO—CH$_2$—C$^{**2}$H[O—CH$_2$—C$_6$H$_5$]—(CH$_2$)$_{10}$—CH$_3$, (3(BnO)C$_{14}$),
—CO—CH$_2$—C$^{**2}$H[O—P(O)(OH)$_2$]—(CH$_2$)$_{10}$—CH$_3$, (3[(OH)$_2$—P(O)O]C$_{14}$).

C$^{1}$ and C$^{2}$ corresponding to asymetric carbons in configuration R, S, or in the racemic form RS, in the formulae mentioned above.

The invention also relates to a method as defined above, wherein the administered compound has the general formula (II):

(II)

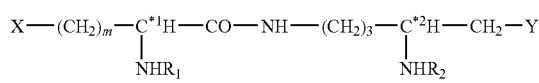

Wherein X, Y, R$_1$, R$_2$, and m are as defined above, C$^{*1}$ is in configuration R, S, or is the racemic RS, and C$^{*2}$ is in configuration R.

The invention relates more particularly to a method as defined above, wherein the administered compound is selected among those of formula (II) wherein:

X=—O—P(O)(OH)$_2$, Y=—O—P(O)(OH)$_2$, R$_1$=—CO—CH$_2$—C$^{1}$H[O—CO—(CH$_2$)$_{10}$—CH$_3$]—(CH$_2$)$_{10}$—CH$_3$, R$_2$=—CO—CH$_2$—C$^{2}$HOH—(CH$_2$)$_{10}$—CH$_3$, m=2, C$^{*1}$ is in configuration S, C$^{*2}$ is in configuration R, C$^{1}$ and C$^{2}$ are in configuration R, i.e. (3S,9R)-3-[(R)-3-dodecanoyloxytetradecanoylamino]-4-oxo-5-aza-9-[(R)-3-hydroxytetradecanoyl amino]-decan-1,10-diol (1,10)-bis-dihydrogenophosphate (OM-294-DP (S,R)), X=—O—P(O)(OH)$_2$, Y=—O—CO—(CH$_2$)$_4$—CHOH—CH$_2$OH, R$_1$=—CO—CH$_2$—C$^{1}$H[O—CO—(CH$_2$)$_{10}$—CH$_3$]—(CH$_2$)$_{10}$—CH$_3$, R$_2$=—CO—CH$_2$—C$^{2}$HOH—(CH$_2$)$_{10}$—CH$_3$, m=2, C$^{*1}$ is in configuration S, and C$^{*2}$ is in configuration R, C$^{1}$ and C$^{2}$ are in configuration R, i.e. (3S, 9R)-3-[(R)-3-dodecanoyloxytetradecanoylamino]-4-oxo-5-aza-9-[(R)-3-hydroxy tetradecanoyl amino]-decan-1, 10-diol 1-dihydrogenophosphate 10-(6,7-dihydroxyheptanoate) (OM-197-MP-HD (S,R)), X=—COOH, Y=—O—CO—(CH$_2$)$_4$—CHOH—CH$_2$OH, R$_1$=—CO—CH$_2$—C$^{1}$H[O—CO—(CH$_2$)$_{10}$—CH$_3$]—(CH$_2$)$_{10}$—CH$_3$, R$_2$=—CO—CH$_2$—C$^{2}$HOH—(CH$_2$)$_{10}$—CH$_3$, m=1, C$^{*1}$ is in configuration S, and C$^{*2}$ is in configuration R, C$^{1}$ and C$^{2}$ are in configuration R, i.e. N-[(R)-3-dodecanoyloxytetradecanoyl]-L-aspartic acid, α-N-{(4R)-5-hydroxy-4-[(R)-3-hydroxytetradecanoylamino]pentyl}amide 5-O-(6,7-dihydroxyheptanoate) (OM-197-MC-HD (S,R)), X=—O—P(O)(OH)$_2$, Y=—O—CO—(CH$_2$)$_5$—NH$_2$, R$_1$=—CO—CH$_2$—C$^{1}$H[O—CO—(CH$_2$)$_{10}$—CH$_3$]—(CH$_2$)$_{10}$—CH$_3$, R$_2$=—CO—CH$_2$—C$^{2}$HOH—(CH$_2$)$_{10}$—CH$_3$, m=2, C$^{*1}$ is in configuration S, and C$^{*2}$ is in configuration R, C$^{1}$ and C$^{2}$ are in configuration R, i.e. (3S,9R)-3-[(R)-3-dodecanoyloxytetradecanoylamino]-4-oxo-5-aza-9-[(R)-3-hydroxytetra decanoylamino]-decan-1,10-diol 1-dihydrogeno phosphate 10-(6-aminohexanoate) (OM-197-MP-AC (S,R)), X=—NH$_2$, Y=—O—P(O)(OH)$_2$, R$_1$=—CO—CH$_2$—C$^{1}$H[O—CO—(CH$_2$)$_{10}$—CH$_3$]—(CH$_2$)$_{10}$—CH$_3$, R$_2$=—CO—CH$_2$—C$^{2}$HOH—(CH$_2$)$_{10}$—CH$_3$, m=4, C$^{*1}$ is in configuration S, and C$^{*2}$ is in configuration R, C$^{1}$ and C$^{2}$ are in configuration R, i.e. (5S,11R)-1-Amino-5-[(R)-3-dodecanoyloxytetradecanoylamino]-6-oxo-7-aza-11-[(R)-3-hydroxytetra decanoylamino]-dodecan-12-ol 12-dihydrogen phosphate (OM-294-BA-MP (S,R)).

The invention also concerns a method as defined above, for treating warm-blooded animals including humans, suffering from a disease or disorder related to an overproduction of inflammatory cytokines or inflammatory disease markers by activated T lymphocytes, monocytes, or antigen presenting cells in the organism, wherein the inflammatory cytokines or inflammatory disease markers belong to the group consisting of IL-1β, IL-4, IL-5 IL-6, IL-8, IL-9, IL-13, IFN-γ, TNF-α, and MCP-1.

The invention relates more particularly to a method as defined above, wherein the disease is selected from the group consisting of asthma, diabetes, atopic dermatitis, allergic rhinitis, prostatitis, inflammatory bowel disease, and rhumatoid arthritis.

The invention also relates more particularly to a method as defined above, which consists in administering a therapeutically effective amount of any compound of formula (I) as defined above of the invention in a pharmaceutically-acceptable carrier, excipient or formulation, via a mucosal or parenteral route.

The invention also concerns more particularly a method as defined above, which consists in administering a therapeutically effective amount of a compound of formula (I) as defined above of the invention preferentially via the peritoneal, subcutaneous, oral, intranasal, sublingual, or aerosol routes.

The invention relates more particularly to gastroresistant pharmaceutical compositions comprising a therapeutically effective amount of a compound of formula (I) as defined above in association with a gastroresistant carrier such as hydrophilic poloxamer surfactants such as poloxamer 407 (Lutrol F-127). Colloidal carriers such as polymeric nanoparticules or microparticules are also appropriate formulations for the oral delivery of formula (I) when enteric polymers such as methacrylate polymers are used.

In a more conventional way the use of gastroresistant tablets or capsules obtained by the use of an enteric coating could also be an alternative for the oral route.

The invention also relates more particularly to a method as defined above, wherein the needed dosages of the immuno-modulatory molecules of formula (I) as defined above of the invention range from 0.01 to 50 mg/m² in humans.

The invention also relates to the use of at least one compound of formula (I) as defined above for the preparation of a drug for the prevention or treatment of a disease or disorder such as asthma, diabetes, atopic dermatitis, allergic rhinitis, prostatitis, inflammatory bowel disease, and rhumatoid arthritis, related to an overproduction of inflammatory cytokines or inflammatory disease markers.

The invention also concerns the compounds of formula (I) as defined above, and the pharmaceutical containing said compounds in association with a physiologically acceptable carrier.

Compounds of formula (I) as defined above of the present invention can be prepared according to the method described in WO 00/00462 and WO 01/46127 relative to the preparation and the use of compounds of formula (I) in the treatment of cancers, or as immunoadjuvants.

The invention will be further described in details in the following description of the synthesis of compounds OM-294-DP (S,R), OM-197-MP-HD (S,R), OM-197-MC-HD (S,R), OM-197-MP-AC (S,R), and OM-294-BA-MP (S,R), and of their biological properties.

EXAMPLES

Example 1

(3S,9R)-3-[(R)-3-dodecanoyloxytetradecanoylamino]-4-oxo-5-aza-9-[(R)-3-hydroxytetradecanoylamino]-decan-1,10-diol 1-dihydrogenophosphate 10-(6-aminohexanoate) (=OM-197-MP-AC (S,R)) (Scheme 1)

1. (2R)-5-(Benzyloxycarbonylamino)-2-[(R)-3-benzyloxytetradecanoylamino]-1-(2-tetrahydropyranyloxy)pentane (C-1)

To a solution of (2R)-5-(benzyloxycarbonylamino)-2-[(R)-3-benzyloxytetra-decanoylamino]pentan-1-ol (PCT WO00146127A1) (2.5 g; 4.39 mmol) in anhydrous $CH_2Cl_2$ (83 ml) at room temperature and under argon were added successively 3,4-dihydro-2H-pyran (DHP) (1.4 ml, 15.38 mmol) then pyridinium p-toluenesulfonate (PPTS) (441 mg, 1.75 mmol). The solution was stirred for 18 h at room temperature then diluted with $CH_2Cl_2$ (100 ml), washed with 5% aqueous $NaHCO_3$ then with $H_2O$. The organic phase was dried over $MgSO_4$, filtered and concentrated. Purification by flash chromatography on silica gel (AcpOEt/pet. ether 4/1) gave compound C-1 (2.86 g; 100%) as a white crystalline solid. (Rf=0.66 in AcOEt/pet. ether 4/1; U.V. and phosphomolybdate).

$C_{39}H_{60}N_2O_6$. IS/MS: m/z 653.5 ([M+H]$^+$), 675.5 ([M+Na]$^+$). Mp=84-86° C.

2. (2R)-5-Amino-2-[(R)-3-benzyloxytetradecanoylamino]-1-(2-tetrahydropyranyloxy)-pentane (C-2)

A solution of compound C-1 (2.5 g; 4.4 mmol) in EtOH (150 ml) containing triethylamine (4 ml) was hydrogenated in the presence of 10% Pd on C at room temperature and under atmospheric pressure of hydrogen for 3.5 h. The catalyst was then removed by filtration, washed with ethanol and the filtrate was concentrated and dried under high vacuum to give the free amine C-2 (2.15 g; 96%) as an amorphous, white solid. $C_{31}H_{54}N_2O_4$. IS/MS: m/z 519.5 ([M+H]$^+$).

3. (S)-(α)-[(R)-3-Dodecanoyloxytetradecanoylamino]-γ-butyrolactone (C-3)

To a solution of (R)-3-dodecanoyloxytetradecanoic acid [Bull. Chem. Soc. Jpn 60 (1987), 2205-2214] (2.16 g; 5.1 mmol) in anhydrous THF (28 ml) at −15° C. and under argon were added successively N-methylmorpholine (0.56 ml; 5.1 mmol; 1 eq) and isobutyl chloroformate (657 µl; 5.1 mmol; 1 eq). After 1 h under stirring at −15° C., L-homoserine lactone hydrobromide (916 mg; 5.1 mmol; 1 eq) as a solution in 0.72 M aqueous $NaHCO_3$ (14 ml, 2 eq) was added. The reaction mixture was stirred for 20 h at room temperature. The mixture was diluted with $Et_2O$ (130 mL), the organic phase was separated and washed with $H_2O$ then dried over $MgSO_4$, filtered and concentrated. A purification by crystallization (minimum volume of $CH_2Cl_2$ and excess pentane at 0° C.) gave compound C-3 (2.17 g; 85%) as a white solid. $C_{30}H_{55}NO_5$. IS/MS: m/z 510.5 ([M+H]$^+$), 532.5 ([M+Na]$^+$). mp=79-80° C.

4. (3S-9R)-3-[(R)-3-Dodecanoyloxytetradecanoylamino]-4-oxo-5-aza-9-[(R)-3-benzyloxytetradecanoylamino]-10-(2-tetrahydropyranyl)oxy-decan-1-ol (C-4)

To a solution of compound C-2 (638 mg, 1.23 mmol, 1.3 eq) in anhydrous $CH_2Cl_2$ (1.5 mL) at 20-21° C. was added compound C-3 (483 mg, 0.95 mmol). The solution was stirred for 3 days at 20-21° C.; the solvent was evaporated under reduced pressure. A purification by flash chromatography on silica gel ($CH_2Cl_2$/acetone 5/1 to 1/1) gave alcohol C-4 (829 mg, 85%) as a white solid. $C_{61}H_{109}N_3O_9$. IS/MS: m/z 1029.0 ([M+H]$^+$), 1051.0 ([M+Na]$^+$). mp=81-82° C.

5. (3S,9R)-3-[(R)-3-Dodecanoyloxytetradecanoylamino]-4-oxo-5-aza-9-[(R)-3-benzyloxytetradecanoylamino]-10-(2-tetrahydropyranyl)oxy-decan-1-ol dibenzyl phosphate (C-5)

To a solution of alcohol C-4 (120 mg; 0.12 mmol) and 1H-tetrazole (25 mg; 0.35 mmol; 3 eq) in anhydrous THF (5 ml) at room temperature and under argon was added N,N-dibenzyl diethylphosphoramidite (85%, 95 µl; 0.27 mmol; 2.3 eq). After 45 min under stirring, the reaction mixture was cooled down to −40° C. then a solution of mCPBA (57-86%; 75 mg; 0.43 mmol; 3.7 eq) in $CH_2Cl_2$ (3 ml) was added. After 45 min at −40° C., the mixture was warmed up and a saturated solution of $Na_2S_2O_3$ (3 ml) was added and the mixture was stirred for 10 min. The solution was diluted with ether, the organic phase was separated and washed with saturated $Na_2S_2O_3$ (5×), then with saturated $NaHCO_3$ (2×). The organic phase was dried over MgSO₄, filtered and concentrated. Purification by flash chromatography on silica gel (CH₂Cl₂/acetone 4/1 then 2/1) gave dibenzyl phosphate C-5 (126 mg; 84%) as an amorphous solid.

6. (3S,9R)-3-[(R)-3-Dodecanoyloxytetradecanoylamino]-4-oxo-5-aza-9-[(R)-3-benzyloxytetradecanoylamino]-decan-1,10-diol 1-(dibenzyl phosphate) (C-6)

To a 1% HCl solution in methanol (25 ml) at 0° C. was added a solution of compound C-5 (700 mg, 0.54 mmol) in CH₂Cl₂ (2.5 ml). After 45 min under stirring at 0° C., the reaction mixture was neutralized with 5% aqueous NaHCO₃, diluted with CH₂Cl₂ then the organic phase was separated. The aqueous phase was extracted with CH₂Cl₂ (3×) then the organic phases were combined, dried over MgSO₄, filtered and concentrated to give alcohol C-6 (640 mg; 98%).

7. (3S,9R)-3-[(R)-3-dodecanoyloxytetradecanoylamino]-4-oxo-5-aza-9-[(R)-3-benzyloxytetradecanoylamino]-decan-1,10-diol 1-dibenzyl phosphate 10-(6-benzyloxycarbonylaminohexanoate (C-7)

To a solution of the compound prepared above C-6 (640 mg, 0.53 mmol.) and 6-(benzyloxycarbonylamino)hexanoic acid (423 mg, 1.60 mmol.) in dry CH₂Cl₂ (25 ml) at 0° C. and under argon flow, there are added in succession commercially available 1-(3-dimethylaminopropyl)-3-ethylcarbodiimide hydrochloride (306 mg, 1.60 mmol.) and 4-dimethylaminopyridine (20 mg, 160 μmol.). The reaction mixture is then stirred for 30 minutes at 0° C. and thereafter overnight at room temperature. The reaction medium is then washed with water and a solution of 1N HCl followed by layer separation. The organic layer is dried over MgSO₄, filtered and evaporated. By running a flash chromatography purification on a silica gel (4/1 then 2/1 CH₂Cl₂/acetone eluent), there is recovered the coupling reaction product C-7 (537 mg; 71%). ¹³C-NMR (62.89 MHz, CDCl₃), δ in ppm: 173.18, 171.16, 170.38, 169.60, 156.30, 138.23, 136.50, 135.38, 135.28, 128.42, 128.26; 128.17, 127.79, 127.74, 127.44, 76.48, 71.15, 70.84, 69.47, 69.39, 69.31, 66.25, 65.62, 64.37, 49.78, 47.76, 41.41, 41.34, 40.57, 38.97, 34.22, 34.16, 33.96, 33.57, 32.95, 31.70, 29.15, 28.95, 28.32, 25.87, 25.46, 25.02, 28.80, 24.18, 22.49, 13.94.

8. (3S,9R)-3-[(R)-3-dodecanoyloxytetradecanoylamino]-4-oxo-5-aza-9-[(R)-3-hydroxytetradecanoylamino]-decan-1,10-diol 1-dihydrogenphosphate 10-(6-aminohexanoate) (C-8) (=OM-197-MP-AC (S,R))

A solution of the compound C-7 (500 mg, 0.35 mmol.) in a 5/2 CH₂Cl₂/ethanol mixture (70 ml) containing acetic acid (10 ml) is hydrogenated in presence of Pd on carbon containing 10% Pd at room temperature and under atmospheric pressure hydrogen for 12 to 24 hours. The catalyst is filtered off. The filtrate is evaporated to dryness and the residue is then dried by suction from a vacuum pump to obtain C-8 (368 mg, quantitative yield). ES/MS: m/z ratio 1047.9 [M+H]⁺; 1069.8

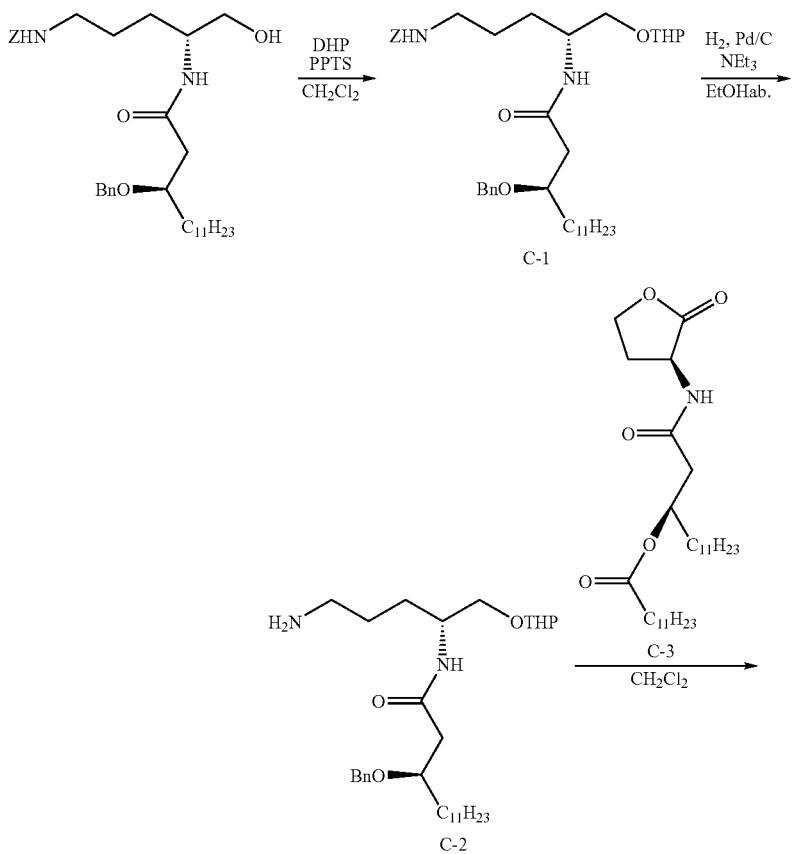

Scheme 1

-continued
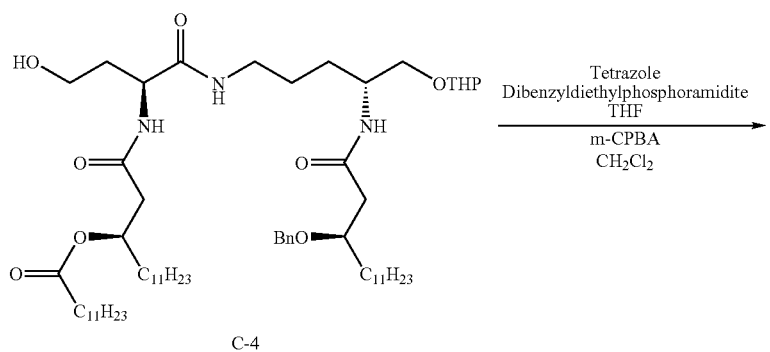
C-4
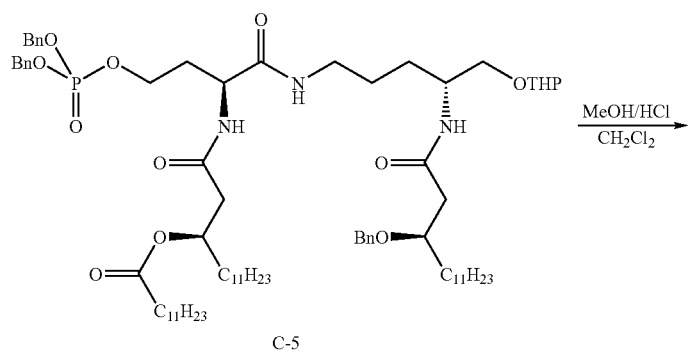
C-5
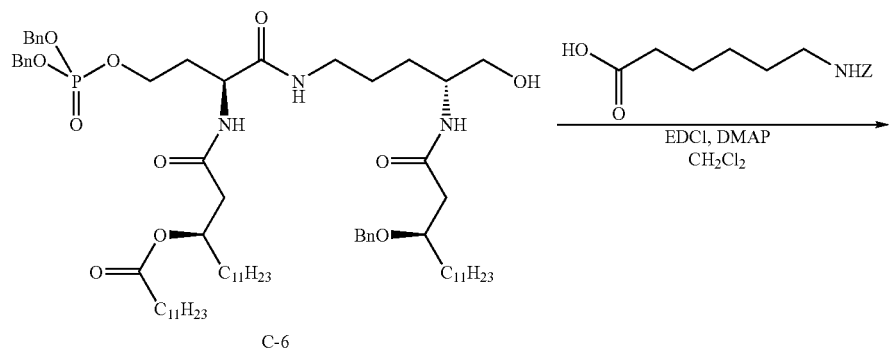
C-6
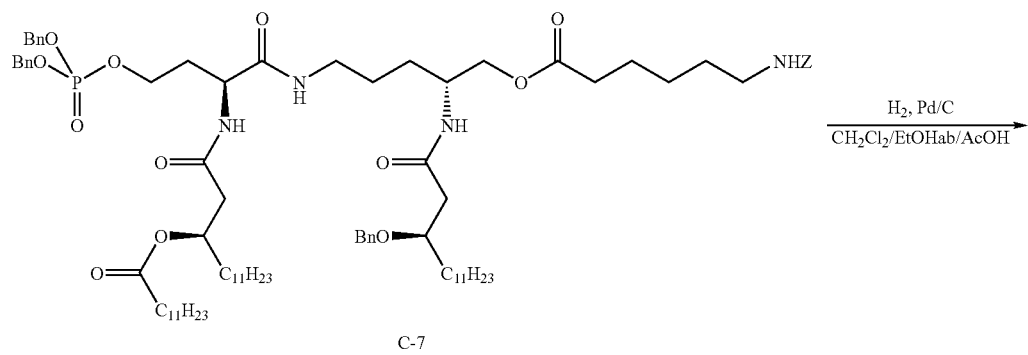
C-7

-continued

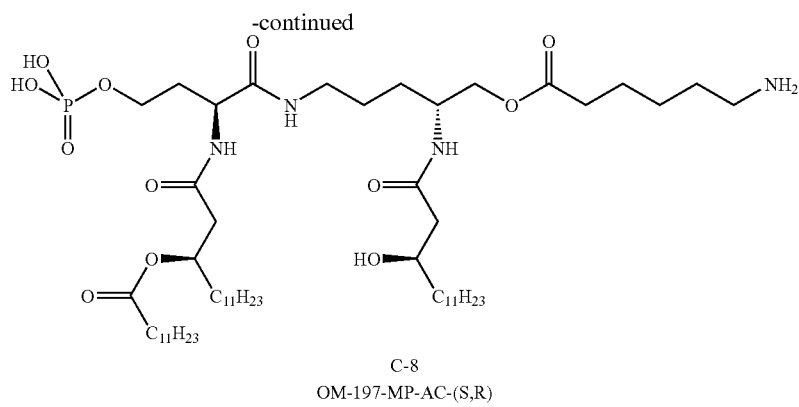

C-8
OM-197-MP-AC-(S,R)

Example 2

(3S,9R)-3-[(R)-3-dodecanoyloxytetradecanoylamino]-4-oxo-5-aza-9-[(R)-3-hydroxytetradecanoylamino]-decan-1,10-diol 1-dihydrogenophosphate 10-(6,7-dihydroxyheptanoate) (=OM-197-MP-HD (S,R)) (Scheme 2)

1. Benzyl 6-heptenoate (C-9)

To a solution of 6-heptenoic acid (4.71 g, 36.75 mmol) in AcOEt (80 mL) at 0° C. were successively added triethylamine (15.3 mL, 110.24 mmol), benzyl bromide (13.1 mL, 110.24 mmol) and Bu$_4$NI (6.79 g, 18.37 mmol). The reaction mixture was stirred at 0° C. for 2H and concentrated in vacuo. The residue is taken up in AcOEt, the organic phase was washed with a saturated aqueous NaHCO$_3$ and H$_2$O. The organic phase was dried over MgSO$_4$ and the solvent removed in vacuo. Flash chromatography of the residue on silica gel (n-heptane/EtOAc, 9:1) provided compound C-9 (6.00 g 75%) as a colorless oil. $^{13}$C-NMR (62.89 MHz, CDCl$_3$): 24.42, 28.34, 33.37, 34.13, 66.08, 114.73, 128.19, 128.55, 136.16, 138.37, 173.43.

2. Benzyl 6,7-epoxyheptanoate (C-10)

To a solution of m-CPBA (2.76 g, 12.29 mmol) in CH$_2$Cl$_2$ (50 mL) at 0° C. was slowly added a solution of C-9 (1.79 g, 8.19 mmol) in CH$_2$Cl$_2$ (20 mL). The solution was stirred at 0° C. for 2H then at room temperature for 18 H. The solution was diluted with CH$_2$Cl$_2$ and the organic phase was washed with a saturated aqueous Na$_2$S$_2$O$_3$ solution (5×). The organic phase was dried over MgSO$_4$ and the solvent removed in vacuo. Flash chromatography of the residue on silica gel (n-heptane/EtOAc, 5:1) provided compound C-10 (1.54 g; 80%) as a colorless oil. $^{13}$C-NMR (62.89 MHz, CDCl$_3$): 24.60, 25.39, 32.00, 34.02, 46.86, 51.91, 66.04, 128.11, 128.46, 136.01, 173.17.

3. Benzyl 6,7-Isopropylideneheptanoate (C-11)

To a solution of C-10 (1.54 g, 6.59 mmol) in acetone (50 mL) at room temperature was added sulfuric acid (0.42 mL, 7.9 mmol). The solution was stirred for 3H, diluted with diethyl ether and the organic phase washed with a saturated aqueous NaHCO$_3$ solution. The organic phase was dried over MgSO$_4$ and the solvent removed in vacuo to give C-11 (1.73 g) as a pale yellow oil which was used in the next step without further purification.

4. 6,7-Isopropylideneheptanoic acid (C-12)

A solution of the compound C-11 (1.53 g) in EtOAc (20 ml) containing Et$_3$N (3.65 mL, 26.16 mmol) was hydrogenated in presence of Pd on carbon containing 10% Pd at room temperature and under atmospheric pressure hydrogen for 3 h. The catalyst is filtered off and the filtrate is evaporated to dryness. Flash chromatography of the residue on silica gel (CH$_2$Cl$_2$/MeOH, 5:1) provided compound C-12 (0.63 g; 54% over 2 steps) as a colorless oil.

5. (3S,9R)-3-[(R)-3-dodecanoyloxytetradecanoylamino]-4-oxo-5-aza-9-[(R)-3-benzyloxytetradecanoylamino]-decan-1,10-diol 1-dibenzyl phosphate 10-(6,7-isopropylideneheptanoate) (C-13)

To a solution of the compound prepared above C-6 (248 mg, 0.21 mmol.) and compound 6,7-Isopropylideneheptanoic acid (C-12) (92 mg, 0.45 mmol.) in dry CH$_2$Cl$_2$ (5 ml) at 0° C. and under argon flow, there are added in succession commercially available 1-(3-dimethylaminopropyl)-3-ethylcarbodiimide hydrochloride (91 mg, 0.47 mmol.) and 4-dimethylaminopyridine (catalytic). The reaction mixture is then stirred for 30 minutes at 0° C. and thereafter overnight at room temperature. The reaction medium is then washed with water and a solution of 1N HCl followed by layer separation. The organic layer is dried over MgSO$_4$, filtered and evaporated. By running a flash chromatography purification on a silica gel (CH$_2$Cl$_2$/MeOH, 99:1), there is recovered the coupling reaction product C-13 (240 mg; 83%). ES/MS: m/z 1390 [M+H]$^+$; 1411 [M+Na]$^+$.

6. (3S,9R)-3-[(R)-3-dodecanoyloxytetradecanoylamino]-4-oxo-5-aza-9-[(R)-3-hydroxytetradecanoylamino]-decan-1,10-diol 1-dihydrogenphosphate 10-(6,7-dihydroxyheptanoate) (C-14) (=OM-197-MP-HD (S,R))

A solution of the compound C-13 (180 mg, 0.13 mmol.) in a 5/2 CH$_2$Cl$_2$/ethanol mixture (21 ml) containing acetic acid (3 ml) is hydrogenated in presence of Pd on carbon containing 10% Pd at room temperature and under atmospheric pressure hydrogen for 12 to 36 hours. The catalyst is filtered off. The filtrate is evaporated to dryness and the residue is then dried by suction from a vacuum pump to obtain C-14 (139 mg, quantitative yield). ES/MS: m/z 1079 [M+H]$^+$; 1101 [M+Na]$^+$.

Scheme 2
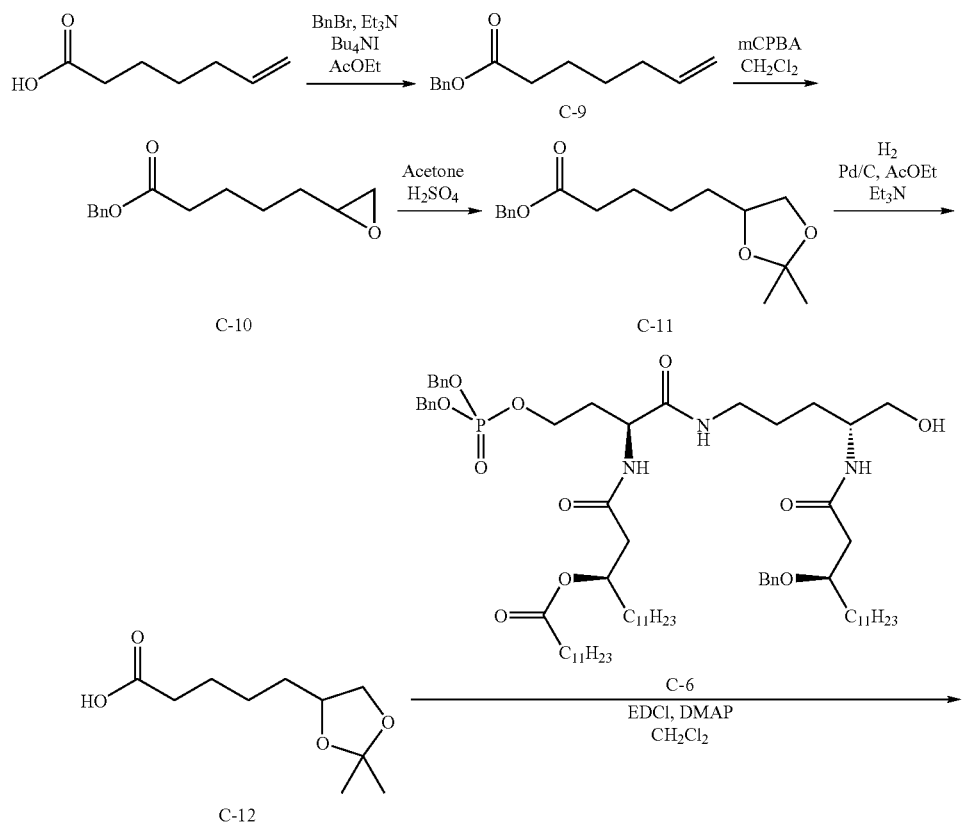
C-10   C-11
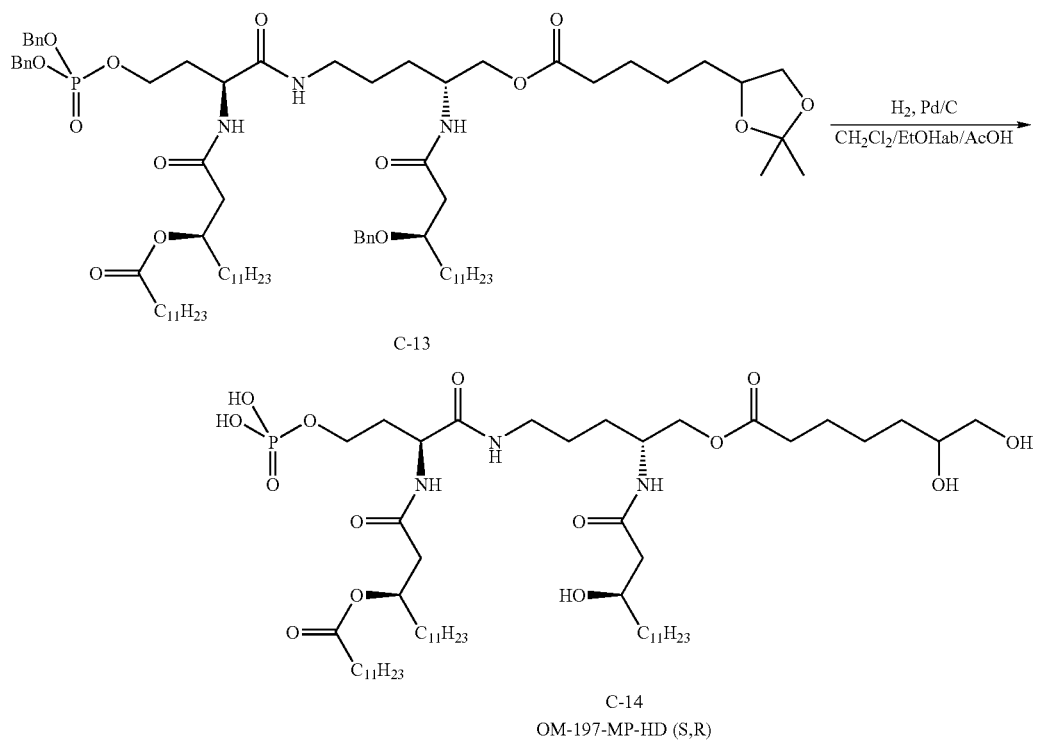
C-13
C-14
OM-197-MP-HD (S,R)

Example 3

(3S,9R)-3-[(R)-3-dodecanoyloxytetradecanoyl-amino]-4-oxo-5-aza-9-[(R)-3-hydroxytetradecanoyl-amino]-decan-1,10-diol 1,10-bis-dihydrogenophosphate) (=OM-294-DP (S,R)) (Scheme 3)

1. (3S,9R)-3-[(R)-3-Dodecanoyloxytetradecanoyl-amino]-4-oxo-5-aza-9-[(R)-3-benzyloxytetrade-canoylamino]-decan-1,10-diol (C-15)

To a solution of (2R)-5-amino-2-[(R)-3-benzyloxytetrade-canoylamino]pentan-1-ol (PCT WO00146127A1) (8 g, 18.4 mmol) in anhydrous $CH_2Cl_2$ (60 mL) at 25° C. was added compound C-3 (9 g, 17.5 mmol) in anhydrous $CH_2Cl_2$ (28 mL). The solution was stirred for 3 days at 20-21° C. The suspension was diluted with $CH_2Cl_2$ (66 mL) and warmed up to 30° C. to obtain a clear solution. Acetonitrile (320 mL) was slowly added to the solution. The solution was cooled down to 20° C. and stirred for 2 H. The precipitate was filtered, washed with acetonitrile and dried under vacuum to obtain C-15 (13.7 g, 83%) as a white solid. mp=103° C.

2. (3S,9R)-3-[(R)-3-Dodecanoyloxytetradecanoyl-amino]-4-oxo-5-aza-9-[(R)-3-benzyloxytetrade-canoylamino]-decan-1,10-diol 1,10-bis-(dibenzyl phosphate) (C-16)

To a solution of C-15 (1.02 g; 1.08 mmol) and 1H-tetrazole (454 mg; 6.48 mmol; 6 eq) in anhydrous THF (46 mL) at room temperature and under argon was added N,N-dibenzyl diethylphosphoramidite (85%, 1.50 mL; 4.97 mmol; 4.6 eq). After 30 min under stirring, the reaction mixture was cooled down to −20° C., then a solution of mCPBA (57-86%; 1.32 g; 7.67 mmol; 7.4 eq) in $CH_2CO_2$ (30 mL) was added. After 45 min at −20° C., the solution was warmed up to 0° C. and a saturated solution of $Na_2S_2O_3$ (25 mL) was added and the mixture was stirred for 10 min. The solution was diluted with ether, the organic phase was separated and washed with saturated $Na_2S_2O_3$ (5×), then with saturated $NaHCO_3$ (2×). The organic phase was dried over $MgSO_4$, filtered and concentrated. Purification by flash chromatography on silica gel ($CH_2Cl_2$/acetone 4/1 then 3/1) gave C-16 (1.38 g; 87%) as colorless oil.

3. (3S,9R)-3-[(R)-3-dodecanoyloxytetradecanoyl-amino]-4-oxo-5-aza-9-[(R)-3-hydroxytetradecanoyl-amino]-decan-1,10-diol 1,10-bis-dihydrogenophosphate) (C-17) (=OM-294-DP (S,R))

A solution of compound C-16 (2.7 g, 1.84 mmol) in isopropanol (150 mL) was hydrogenated over 10% Pd on C (320 mg) at room temperature and under atmospheric pressure of hydrogen for 3 h. The catalyst was removed by filtration through a millipore membrane. The filtrate was concentrated and dried under high vacuum to give C-17 (1.8 g; 98%) as an amorphous solid.

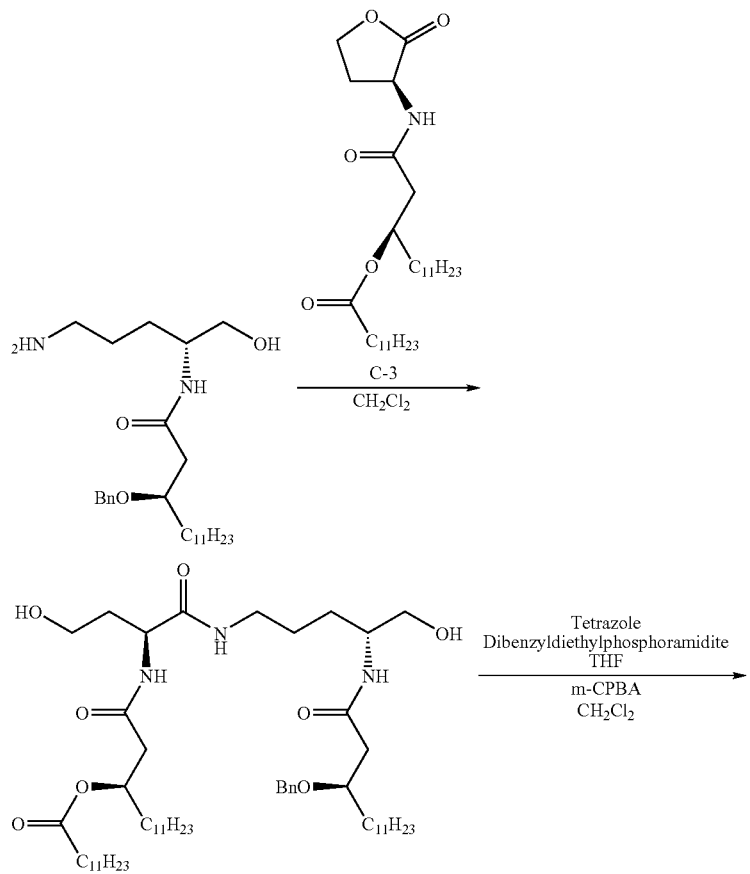

Scheme 3

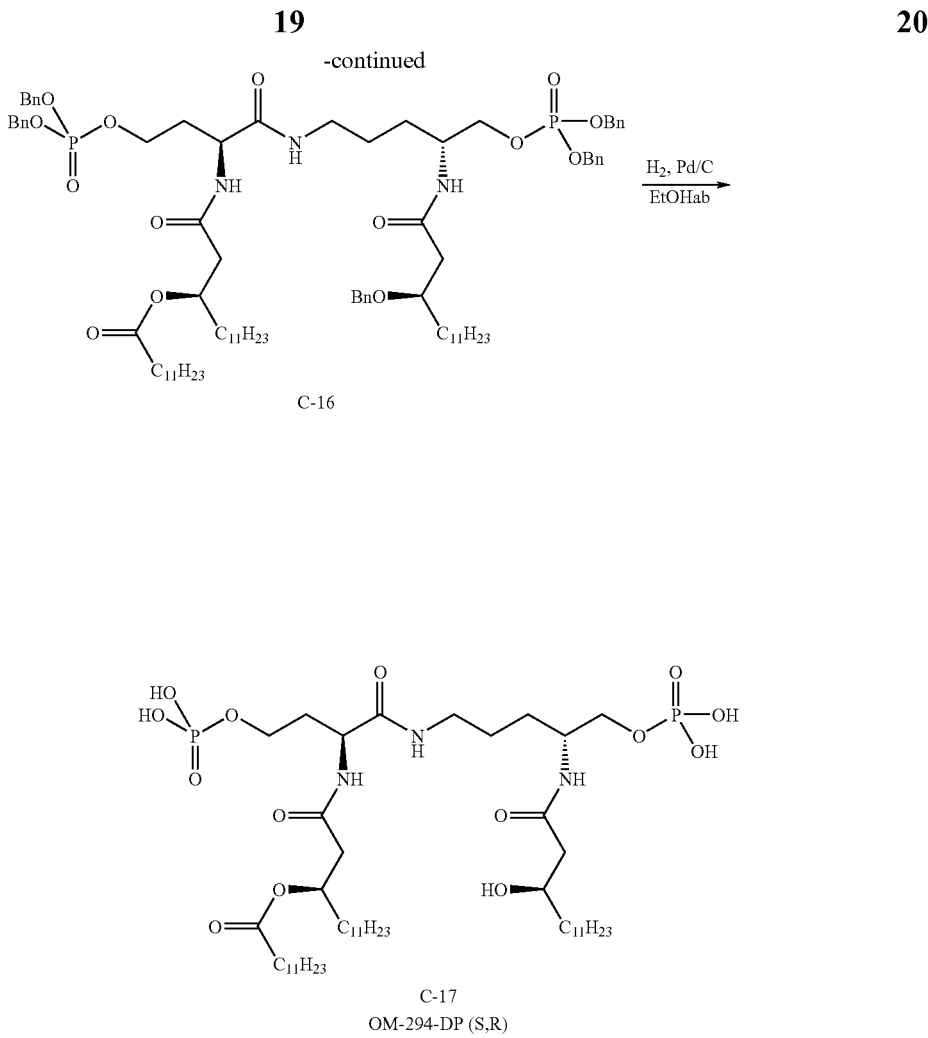

C-16

C-17
OM-294-DP (S,R)

Example 4

N-[(R)-3-dodecanoyloxytetradecanoylamino]-L-aspartic acid, α-N-{(4R)-5-hydroxy-4-[(R)-3-hydroxytetradecanoylamino]-pentyl}amide 5-O-(6,7-dihydroxyheptanoate) (=OM-197-MC-HD (S,R)) (Scheme 4)

1. N-[(R)-3-dodecanoyloxytetradecanoylamino]-L-aspartic acid, α-N-{(4R)-5-hydroxy-4-[(R)-3-benzyloxytetradecanoylamino]pentyl}amide-β-benzyl ester, 5-O-(6,7-isopropylideneheptanoate) (C-18)

To a solution of the compound N-[(R)-3-dodecanoyloxytetradecanoylamino]-L-aspartic acid, α-N-{(4R)-5-hydroxy-4-[(R)-3-benzyloxytetradecanoylamino]pentyl}amide-β-benzyl ester (PCT WO00146127A1) (1.14 g, 1.09 mmol.) and compound 6,7-Isopropylideneheptanoic acid (C-12) (487 mg, 2.48 mmol.) in dry CH$_2$Cl$_2$ (30 mL) at 0° C. and under argon flow, there are added in succession commercially available 1-(3-dimethylaminopropyl)-3-ethylcarbodiimide hydrochloride (485 mg, 2.53 mmol.) and 4-dimethylaminopyridine (43 mg, 0.35 mmol). The reaction mixture is then stirred for 30 minutes at 0° C. and thereafter overnight at room temperature. The reaction medium is then washed with water and a solution of 1N HCl followed by layer separation. The organic layer is dried over MgSO$_4$, filtered and evaporated. By running a flash chromatography purification on a silica gel (CH$_2$Cl$_2$/Acetone, 9:1), there is recovered the coupling reaction product C-18 (1.20 g; 76%) as a white solid.

ES/MS: m/z 1255 [M+Na]$^+$.

2. N-[(R)-3-dodecanoyloxytetradecanoylamino]-L-aspartic acid, α-N-{(4R)-5-hydroxy-4-[(R)-3-hydroxytetradecanoylamino]-pentyl}amide 5-O-(6,7-dihydroxyheptanoate) (C-19) (=OM-197-MC-HD (S,R))

A solution of the compound C-18 (1.20 g, 0.97 mmol.) in a 2/1 CH$_2$Cl$_2$/ethanol mixture (50 mL) containing acetic acid (5 mL) is hydrogenated in presence of Pd on carbon containing 10% Pd at room temperature and under atmospheric pressure hydrogen for 12 to 36 hours. The catalyst is filtered off. The filtrate is evaporated to dryness and the residue is then dried by suction from a vacuum pump to obtain C-19 (1 g, quantitative yield). ES/MS: m/z 1012 [M+H]$^+$; 1034 [M+Na]$^+$.

Scheme 4

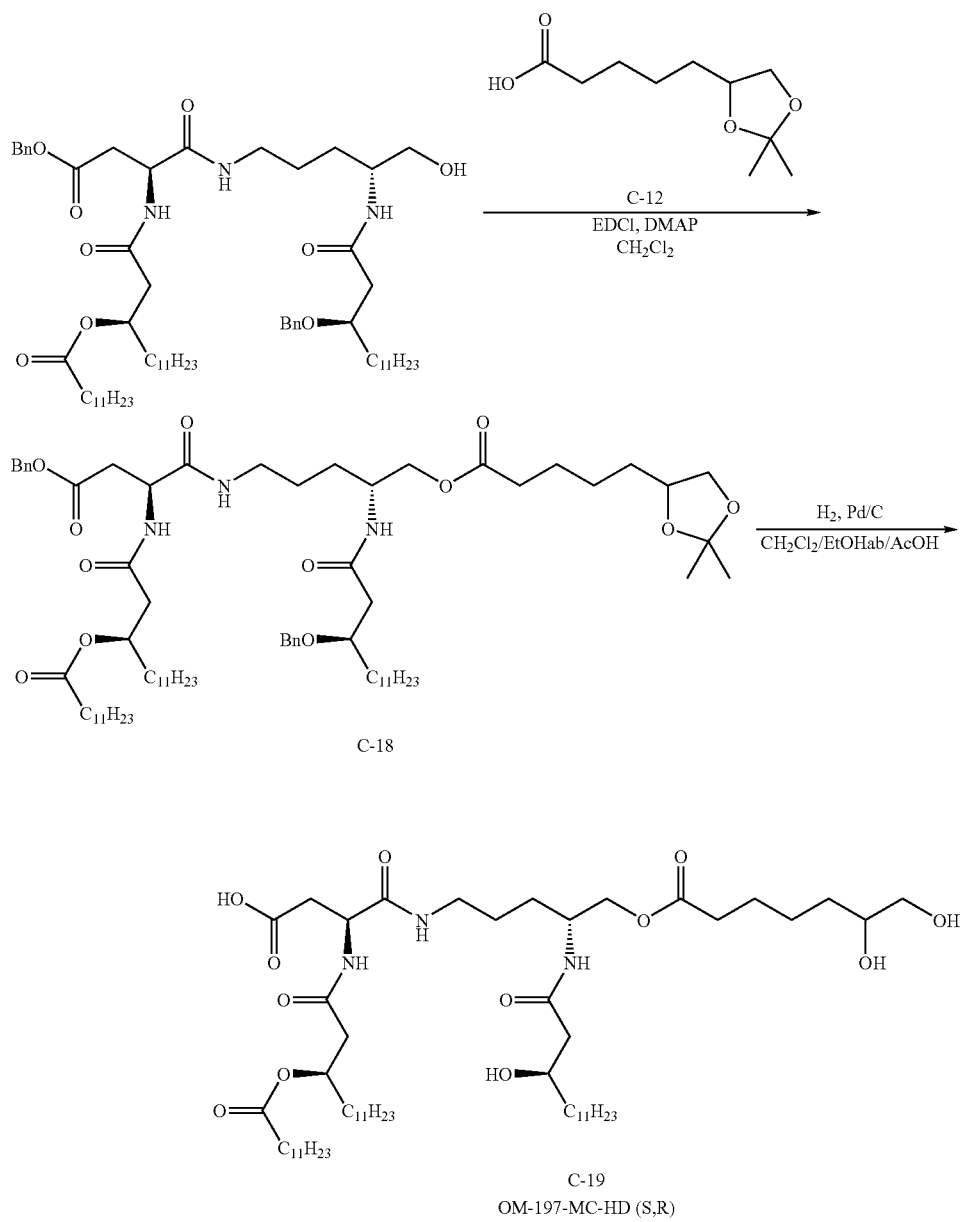

C-19
OM-197-MC-HD (S,R)

Example 5

(5S,11R)-1-Amino-5-[(R)-3-dodecanoyloxytetrade-canoylamino]-6-oxo-7-aza-11-[(R)-3-hydroxytetradecanoylamino]-dodecan-12-ol 12-dihydrogenophosphate (=OM-294-BA-MP (S,R)) (Scheme 5)

1. $N^\alpha$—[(R)-3-Dodecanoyloxytetradecanoyl] $N^\epsilon$-benzyloxycarbonyl-L-lysine (C-20)

To a solution of (R)-3-dodecanoyloxytetradecanoic acid P-109 [Bull. Chem. Soc. Jpn 60 (1987), 2205-2214] (153 mg; 0.36 mmol) in anhydrous THF (4 ml) at −15° C. and under argon were added successively N-methylmorpholine (40 µl; 0.36 mmol 1 eq) and isobutyl chloroformate (47 µl; 0.36 mmol; 1 eq). After 30 min under stirring at −15° C., a solution of commercially available H-L-Lysine(Z)-OH (100 mg; 0.36 mmol; 1 eq) in CH$_3$CN/H$_2$O (3.5/1 (4.5 mL) containing Et$_3$N (0.16 mL) was added. The reaction mixture was stirred for 20 h at room temperature. The organic solvent was then evaporated and the aqueous layer was cooled down to 0° C., acidified with a 10% aqueous solution of citric acid down to pH=3 and extracted with AcOEt (3×). The organic layer was dried over MgSO$_4$, filtered and evaporated. By running a flash chromatography purification on a silica gel (1/1 petroleum ether/AcOEt eluent containing 0.25% of acetic acid) followed by coevaporation of toluene gave C-20 (172 mg; 70%) as a white crystalline solid. MS: (IS+) m/z 690.0 [M+H]$^+$, 707.0 [M+NH$_4$]$^+$, 712.0 [M+Na]$^+$, 727.5 [M+K]$^+$. $^{13}$C-NMR (62.89 MHz, CDCl$_3$), δ in ppm: 174.90, 173.73, 170.66, 156.98, 136.53, 128.57, 128.17, 128.05, 71.27, 66.79, 52.24, 41.32, 40.47, 34.59, 34.24, 31.99, 31.45, 29.72, 29.43, 29.25, 25.29, 25.07, 22.76, 22.27, 14.19.

2. (5S,11R)-1-Benzyloxycarbonylamino-5-[(R)-3-dodecanoyloxytetradecanoyl-amino]-6-oxo-7-aza-11-[(R)-3-benzyloxytetradecanoylamino]-dodecan-12-ol (C-21).

To a solution of C-20 (150 mg; 0.22 mmol.) and (2R)-5-amino-2-[(R)-3-benzyloxy-tetradecanoylamino]pentan-1-ol WZ-10b (PCT WO00146127 A1) (95 mg; 0.22 mmol.; 1.0 eq) in anhydrous CH$_2$Cl$_2$ (3 ml) at 0° C. was added commercially available HOAt (1-hydroxy-7-azabenzotriazol) (36 mg, 0.26 mmol., 1.2 eq.) and commercially-available N,N'-diisopropylcarbodiimide (41 μl, 0.22 mmol., 1.2 eq.). The reaction mixture was stirred for 1 hour at 0° C. and thereafter overnight at room temperature. The reaction mixture was subsequently washed with water, a 1N HCl solution, and a saturated solution of NaHCO$_3$ followed by layer separation. The organic layer was dried on MgSO$_4$, filtered and evaporated. By running a flash chromatography purification on a silica gel (3/1 CH$_2$Cl$_2$/acetone eluent), there was recovered C-21 (165 mg; 68%) as a white crystalline solid. MS: (IS+) m/z 1105.8 [M+H]$^+$, 1128.0 [M+Na]$^+$, $^{13}$C-NMR (62.89 MHz, CDCl$_3$), δ in ppm: 173.56, 172.20, 171.87, 170.23, 156.82, 138.32, 136.69, 128.53, 128.47, 128.09, 128.00, 127.91, 127.82, 76.77, 71.48, 71.15, 66.59, 64.77, 53.1, 51.39, 41.71, 41.63, 40.46, 39.45, 34.57, 34.51, 34.12, 31.97, 29.70, 29.51, 29.41, 29.25, 28.69, 25.38, 25.29, 25.19, 25.09, 22.74, 22.50, 14.18.

3. (5S,11R)-1-Benzyloxycarbonylamino-5-[(R)-3-dodecanoyloxytetradecanoylamino]-6-oxo-7-aza-11-[(R)-3-benzyloxytetradecanoylamino]-dodecan-12-ol 12-dibenzyl phosphate (C-22)

To a solution of C-21 (150 mg; 0.14 mmol) and 1H-tetrazole (29 mg; 0.41 mmol; 3, eq) in anhydrous THF (8 mL) at room temperature and under argon was added N,N-dibenzyl diethylphosphoramidite (85%, 110 μL; 0.31 mmol; 2.3 eq). After 30 min under stirring, the reaction mixture was cooled down to −20° C., then a solution of mCPBA (57-86%; 87 g; 0.50 mmol; 3.7 eq) in CH$_2$Cl$_2$ (6 mL) was added. After 45 min at −20° C., the solution was warmed up to 0° C. and a saturated solution of Na$_2$S$_2$O$_3$ (5 mL) was added and the mixture was stirred for 10 min. The solution was diluted with ether, the organic phase was separated and washed with saturated Na$_2$S$_2$O$_3$ (5×), then with saturated NaHCO$_3$ (2×). The organic phase was dried over MgSO$_4$, filtered and concentrated. Purification by flash chromatography on silica gel (CH$_2$Cl$_2$/acetone 4/1 then 2/1) gave C-22 (149 mg; 81%) as a amorphous solid. MS: (IS+) m/z 1366.0 [M+H]$^+$, 1383.5 [M+NH$_4$]$^+$, 1388.5 [M+Na]$^+$, 1088.0 [M-(BnO)$_2$OPOH)+H]$^+$, $^{13}$C-NMR (62.89 MHz, CDCl$_3$), δ in ppm: 173.51, 171.77, 171.27, 169.95, 156.67, 138.32, 136.69, 135.66 (d), 135.55 (d), 128.69, 128.51, 128.43, 128.03, 127.77, 127.69, 76.49, 71.28, 71.20, 69.66 (d), 69.58 (d), 68.72 (d), 66.51, 52.82, 48.62 (d), 41.76, 41.46, 40.46, 39.01, 34.54, 34.06, 31.96, 29.68, 29.49, 29.39, 29.22, 27.95, 25.29, 25.18, 25.05, 22.73, 22.45, 14.17.

4. (5S,11R)-1-Amino-5-[(R)-3-dodecanoyloxytetradecanoylamino]-6-oxo-7-aza-11-[(R)-3-hydroxytetradecanoylamino]-dodecan-12-ol 12-dihydrogenophosphate (C-23) (=OM-294-BA-MP (S,R))

A solution of the compound C-22 (130 mg, 0.095 mmol.) in a 3/1 CH$_2$Cl$_2$/ethanol mixture (20 mL) containing acetic acid (3 mL) is hydrogenated in presence of Pd on carbon containing 10% Pd at room temperature and under atmospheric pressure hydrogen for 36 hours. The catalyst is filtered off. The filtrate is evaporated to dryness and the residue is then dried by suction from a vacuum pump to obtain C-23 (84 mg, 91%). MS: (IS+) m/z 962.0 [M+H]$^+$, 984.0 [M+Na]$^+$.

Scheme 5

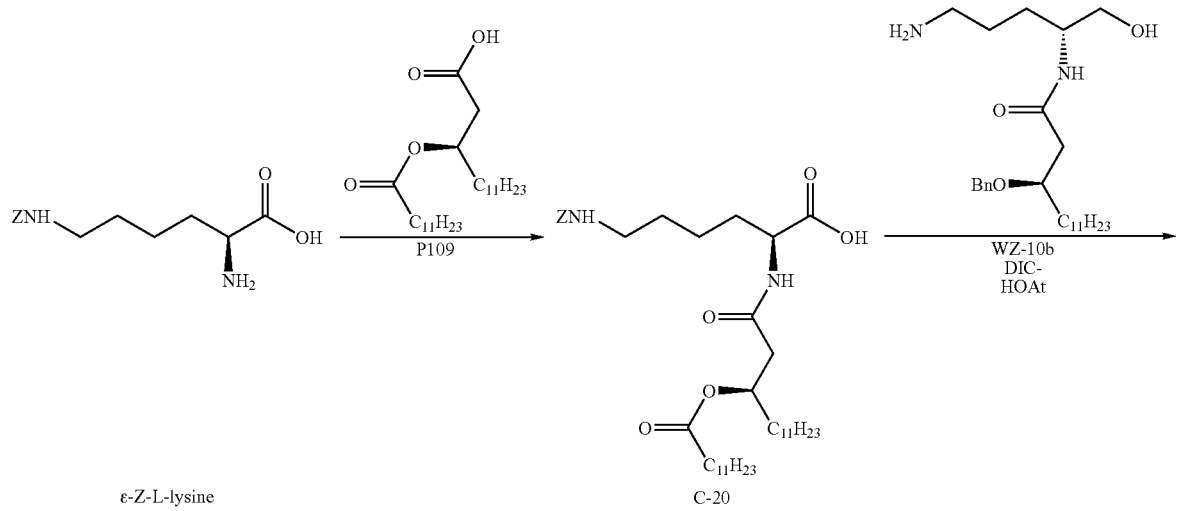

ε-Z-L-lysine                    C-20

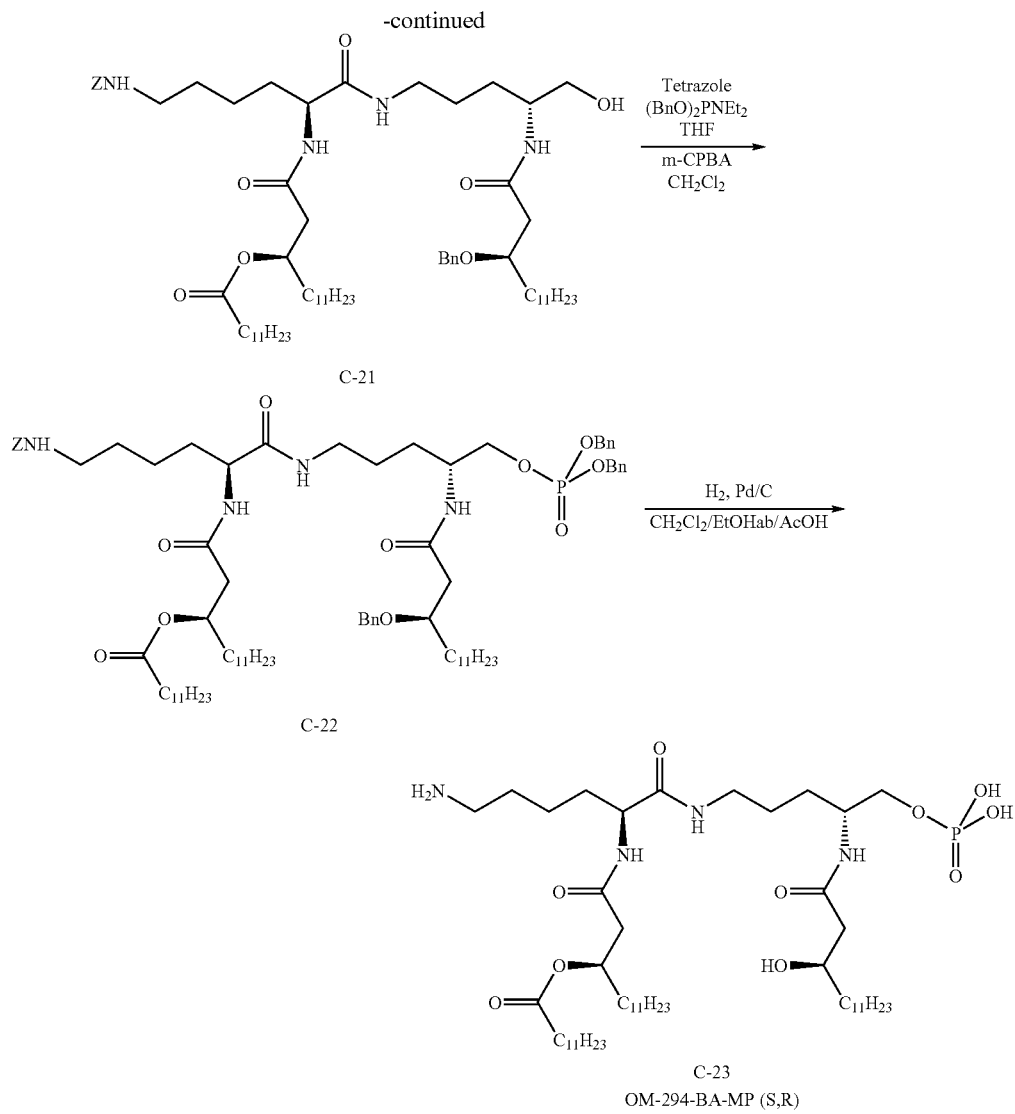

Biological Activities of the Compounds According to the Invention

Example 6

In vitro Regulatory Effect of OM-197-MP-AC and OM-294-DP on LPS Induced Inflammatory (IL-12 and TNF-α) and Anti-inflammatory (IL-10) Cytokines on Murine DC Cells Protocol:

Bone marrow cells were isolated and cultured as described below:

Femora and tibiae from two male C57BL/7, 6 week-old (Charles River Laboratories France), were removed, stripped of muscles and tendons, and desinfected with 70% ethanol. Both ends of each bone were cut and the marrow was flushed with HBSS (Gibco BRL) using a syringe with a 26-gauge needle. The resulting cell suspension was centrifuged for 5 min. at 500 g and washed in HBSS. The cells were resuspended at $3 \times 10^5$ cells/ml in RPMI-1640 (Gibco BRL) supplemented with 2 mM L-glutamin (Sigma), 100 U/ml penicillin (Sigma), 100 μg/ml streptomycin (Sigma), 50 μM β-mercaptoethanol (Sigma), 10% heat-inactivated FCS (Sigma) and 15 ng/ml murine rGM-CSF (R&D).

To generate bone marrow (BM) derived dendritic cells (DC), BM leukocytes were cultured in 100-mm bacteriological petri dishes (Falcon 1029) for 8 days at 37° C. in 5% $CO_2$. On day 0, 10 ml of cell suspension were seeded per dish. On day 3, another 10 ml of freshly prepared medium were added to each plate and on day 6, 9 ml of top medium were carefully removed from each plate and replaced by 10 ml of fresh medium.

Non-adherent cells of the 8-day old BM cell cultures were collected, centrifuged for 5 min. at 500 g, and resuspended at $1.25 \times 10^6$ cells/ml in supplemented RPMI containing 10 ng/ml GM-CSF. The cells were then seeded in 24-well tissue culture plates ($1 \times 10^6$ cells/well) and incubated for 1 h 30 at 37° C. in 5% $CO_2$ in the absence or presence of OM-294-DP or OM-197-MP-AC (0.01-100 μg/ml/200 μl/well). LPS (*E. coli* O26:B6, Sigma), was then added at 1 μg/ml, and the plates were further incubated. After 20 h incubation, the supernatants were collected for analysis of cytokines. IL-12p70, IL-10, and TNF-α concentrations in DC culture supernatants were measured by ELISA using OptElA matched Ab pairs from BD Pharmingen. Supersignal ELISA Pico chemiluminescent peroxidase substrate (BD Pharmingen) was used for the detection by luminometry (Wallac 1420 multilabel counter Victor-2). The assays were performed according to manufacturer's instructions.

Results:

a) Effect of OM-197-MP-AC and OM-294-DP on LPS-Induced IL-12 and IL-10 Production.

Figure 1:
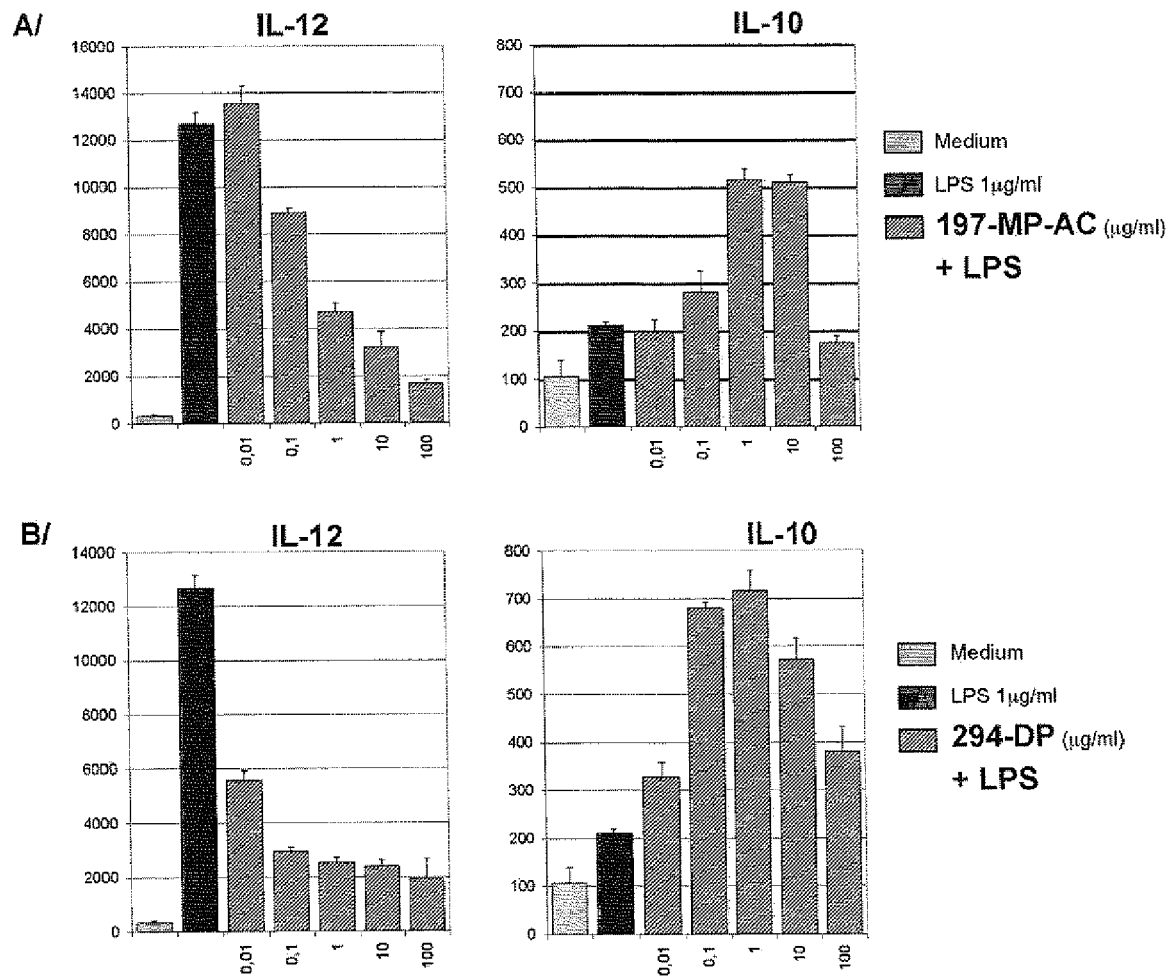

The results on LPS-induced IL-12 and IL-10 production are shown in the FIG. 1.

b) Effect of OM-197-MP-AC and OM-294-DP on LPS-Induced TNF-α Production.

Figure 2:
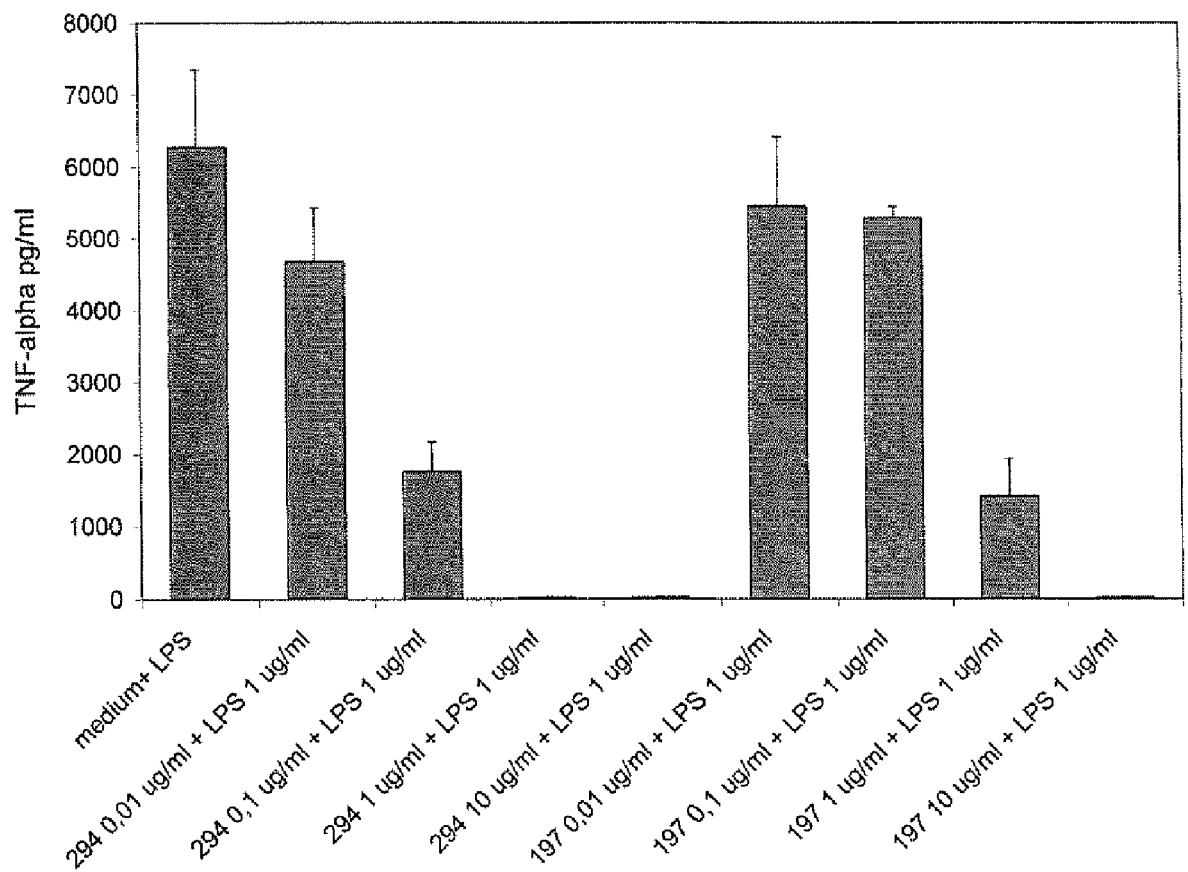

The results on LPS-induced TNF-α production are shown in the FIG. 2.

Conclusion:

The above results clearly show that both OM-197-MP-AC and OM-294-DP decrease the LPS-induced production of the inflammatory cytokines (IL-12 and TNF-α), and in striking contrast increase the production of the anti-inflammatory cytokine IL-10, suggesting that the compounds of the invention could act as therapeutic anti-inflammatory agents.

Example 7

Direct Effects of a Series of Four Triacylated Derivatives on Human $CD4^+$ T Cells Protocol A series of four compounds of the present invention (OM-197-MP-AC, OM-197-MC-HD, OM-294-BA-MP, OM-197-MP-HD) were tested directly as summarized below: Naïve $CD4^+$ T cells were magnetically sorted from healthy blood donor (buffy coat). The cells were stimulated in the presence or not of graded doses of triacyl derivatives (0.02; 0.2; 2 and 20 µg/ml) using plate-bound anti-CD3 (5 µg/ml) and soluble anti-CD28 (1 µg/ml). After 6 days, cytokine levels (IFN-γ and IL-13) were tested in the culture supernatants using ELISA.

Results:

The results for the cytokines production are shown in the FIG. 3. T cell proliferation was also tested but was not modified be the compounds of the invention.

Conclusion:

IL-13 production (white histograms) by $CD4^+$ T cells is reduced in the presence of OM-197-MP-AC, OM-197-MC-HD, OM-294-BA-MP, OM-197-MP-HD whereas IFN-γ production (dark histograms) and T cell proliferation remain unaffected. This represents a shift towards a Th1 response in the presence of the four triacylated molecules tested.

Example 8

Effect of OM-197-MP-AC in a Model of Asthma

Since in the previous example it has been shown that the triacylated molecules tested decreased the production of a cytokine likely involved in the pathology of asthma (i.e. IL-13) the inventors aimed here at investigating in vivo the effects of a member of the series (OM-197-MP-AC) in the modulation of Th2 differentiation of naïve T helper cells and the subsequent development of allergic asthma.

In the present study, the inventors have investigated first (part a) the effect of OM-197-MP-AC given during the sensitization phase on the development of LACK-induced allergic asthma, and then the effect of the molecule tested therapeutically (part b).

Part a) "Prophylactic" Treatment of Asthma

Protocol:

Mice and Induction of Allergic Asthma:

Females Balb/c ByJ mice of 6-week old were purchased from the Centre d'Elevage Janvier (CERJ, Le Genest-St-lsle, France). All the mice were sensitised by 2 i.p. injections of 10 µg LACK protein precipitated in 2 mg of Alum (PerBio Science France SAS, Brebières, France) at days 0 and 7.

Animals were divided in groups, as follow:
LACK-sensitized and saline-challenged mice (4 mice)
LACK-sensitized and challenged mice (8 mice)
OM-197-MP-AC-treated, LACK-sensitized and challenged mice (8 mice)

Mice of the third group were treated intraperitoneally with 1 mg/Kg (20 µg per mouse) of OM-197-M P-AC. Mice were treated on days: −1, 1, 2, 3, 6, 8, 9, 10 and 11. From day 16 to day 21, mice of groups B and C were exposed to a daily 20-min aerosol challenge of a LACK solution (0.15%) whereas mice of the saline group received a saline solution as control.

Airway Hyperresponsiveness (AHR):

AHR was measured for all the mice one day after the last antigen challenge by whole-body plethysmography (Emka) in response to increasing concentrations (6-25 mg/ml) of inhaled methacholine (acetyl methyl choline, Sigma). AHR is expressed as enhanced pause (Penh, see FIG. 4), a dimensionless parameter perfectly correlated to airway compliance and resistance calculated value, which correlates with measurement of airway resistance, impedance, and intrapleural pressure.

Reagents:
LACK recombinant protein was produced in *E. coli* and purified as described by Mougneau et al., 1995.
OM-197-MP-AC, batch DL040906 at the concentration of 0.98 mg/ml, was from OM PHARMA.
Anti-IgE EM-95 mAbs were a gift from DNAX (Palo Alto, Calif., USA).
Methacholine (acetyl methyl choline) was purchased from Sigma (Saint Quentin Fallavier, France).
CBA array beads (Flex set) were purchased from BD Biosciences.

Antibody Titers:

All the mice were bled by heart puncture one day after the last aerosol. Total IgE were quantified by ELISA using rat EM-95 anti-IgE mAbs as coating antibody and rat anti-IgE mAbs coupled to biotin as second antibody as described (Julia et al., 2002).

Analysis of Bronchoalveolar Lavage (BAL) Cells (Percentage of Eosinophils):

Individual mice were bled and a canula was inserted into their trachea. Lungs were washed 3 times with 1 ml of warmed PBS. Cells were washed with PBS, resuspended in 300 µl, and counted using a Burker-Türk chamber. For differential BAL cell counts, cytospin preparations were made and stained with Wright/Giemsa coloration. The respective numbers of neutrophils, eosinophils, and other mononuclear cells were determined by microscopic examination. Only the percentage of eosinophils (FIG. 5) is reported here.

Analysis of Lung Cytokine Contents:

To investigate lung cytokine contents of treated and untreated animals, protein extracts were prepared from lungs of LACK-sensitized and PBS-challenged wt mice (group "Control"), LACK-sensitized and challenged wt mice (group "Asthma"), OM-197-MP-AC-treated wt mice (group "OM-197"). IL-4, IL-5, IL-13 contents were analyzed by multiplex analysis using FACSArray.

Results:
Measurement of Airway Hyperresponsiveness (AHR):

Treated or untreated LACK-sensitized mice (see above) were next challenged with daily aerosol of LACK for five consecutive days. One day after the last aerosol, AHR was measured by whole-body plethysmography in response to increasing concentrations of aerosolized methacholine.

Figure 4:
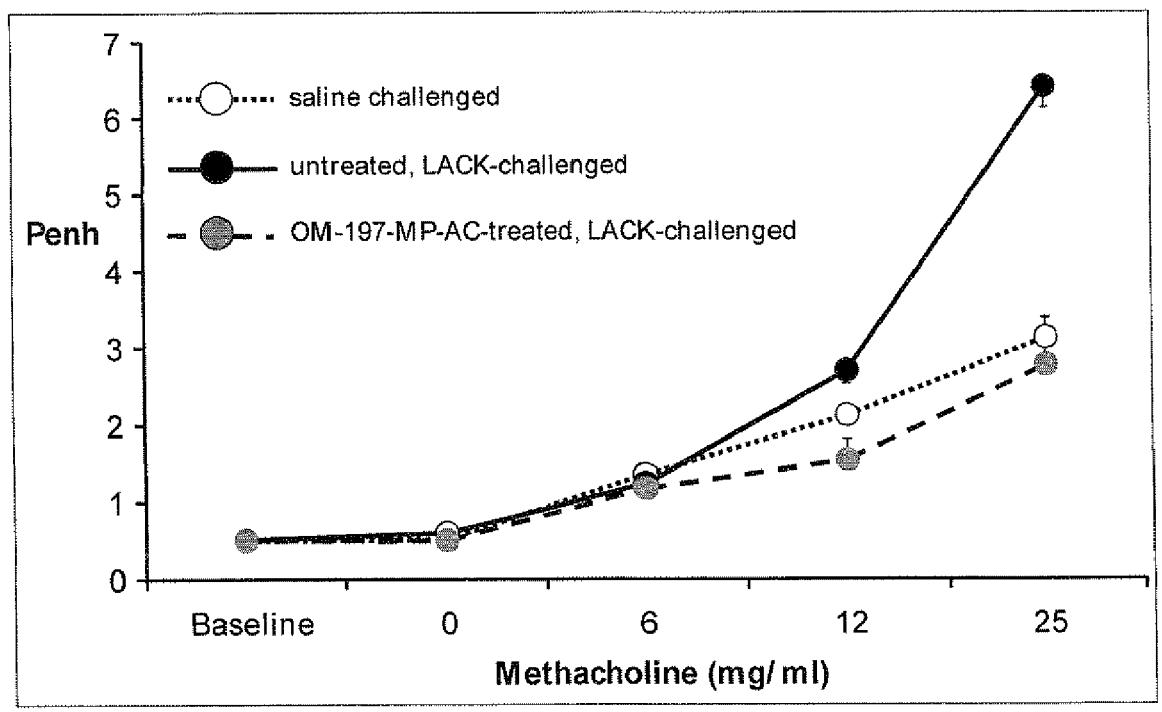

As expected, LACK-sensitized and saline-challenged mice did not develop AHR when exposed to methacholine whereas untreated LACK-sensitized and challenged mice developed a strong AHR, as reflected by high Penh values (FIG. 4). In sharp contrast, LACK-sensitized and challenged mice that were treated with OM-197-MP-AC did not exhibit AHR.

Conclusion:

Airway hyper-responsiveness on exposure of mice to aerosol antigen, measured in the presence of methacholine, was reduced back to control levels (saline) by treatment with OM-197-MP-AC.

Figure 5:
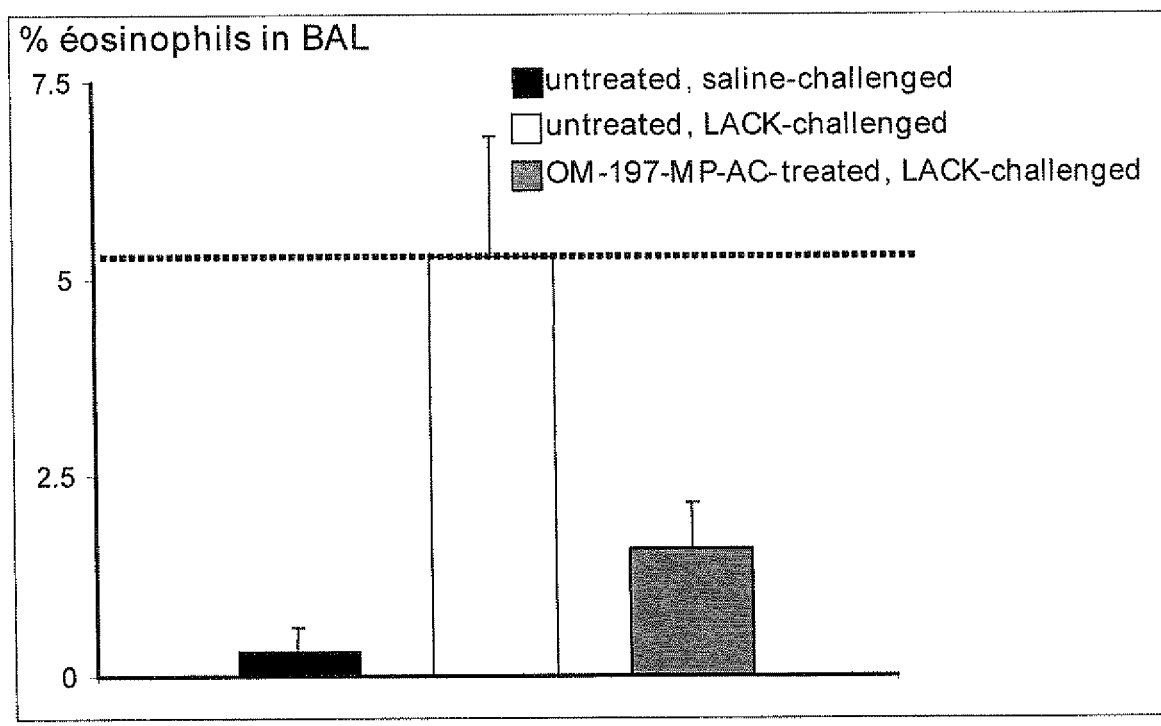

Characterization of the Percentage of Eosinophils in Broncho-Alveolar Ravages (BAL):

The results are reported in FIG. 5.

LACK-sensitized mice that received saline aerosols, did not exhibit eosinophils in BAL whereas LACK-sensitized mice that received LACK aerosol challenges did. In addition, OM-197-MP-AC-treated mice exhibited 3-times less eosinophils, than untreated control mice (FIG. 5).

Conclusion:

Treatments with OM-197-MP-AC strongly decreased BAL eosinophilia.

Figure 6:
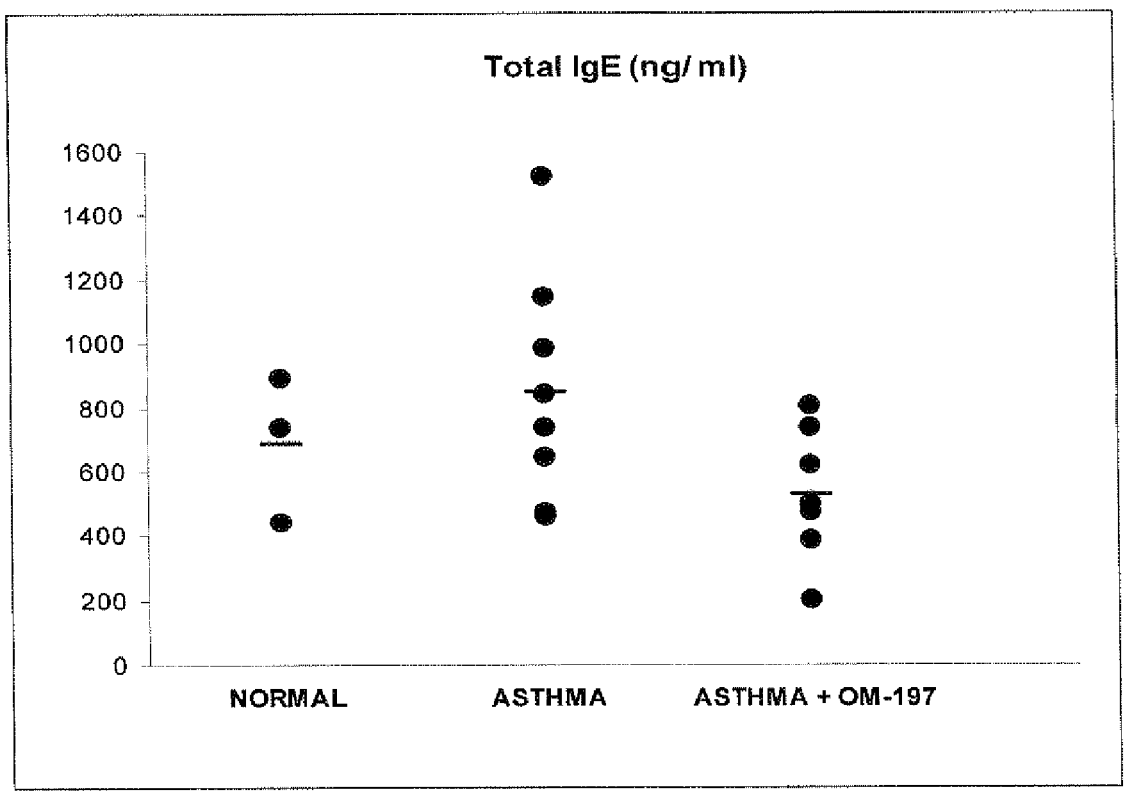

Measurement of Immunoglobulins (Ig) in Sera:

The results for IgE are shown in FIG. 6:

Titers of total IgE (FIG. 6) were significantly decreased when mice were treated with OM-197-MP-AC compound.

Conclusion:

Thus, sera of mice treated with OM-197-MP-AC contained 2-fold less total IgE as compared to sera of untreated sensitized, challenged mice (i.e. "asthmatic animals").

Measurement of Lung Cytokines:

To further investigate the effects of prophylactic OM-197-MP-AC on allergic airway inflammation, proteins were extracted from lungs of both treated and untreated WT mice, and cytokines known to play a important role in asthma (IL-4, IL-5 and IL-13) were quantified by multiplex analysis using CBA array beads and FACSarray. Data were normalized to the total quantity of proteins and given as pg of cytokine per mg of lung proteins.

Figure 7:
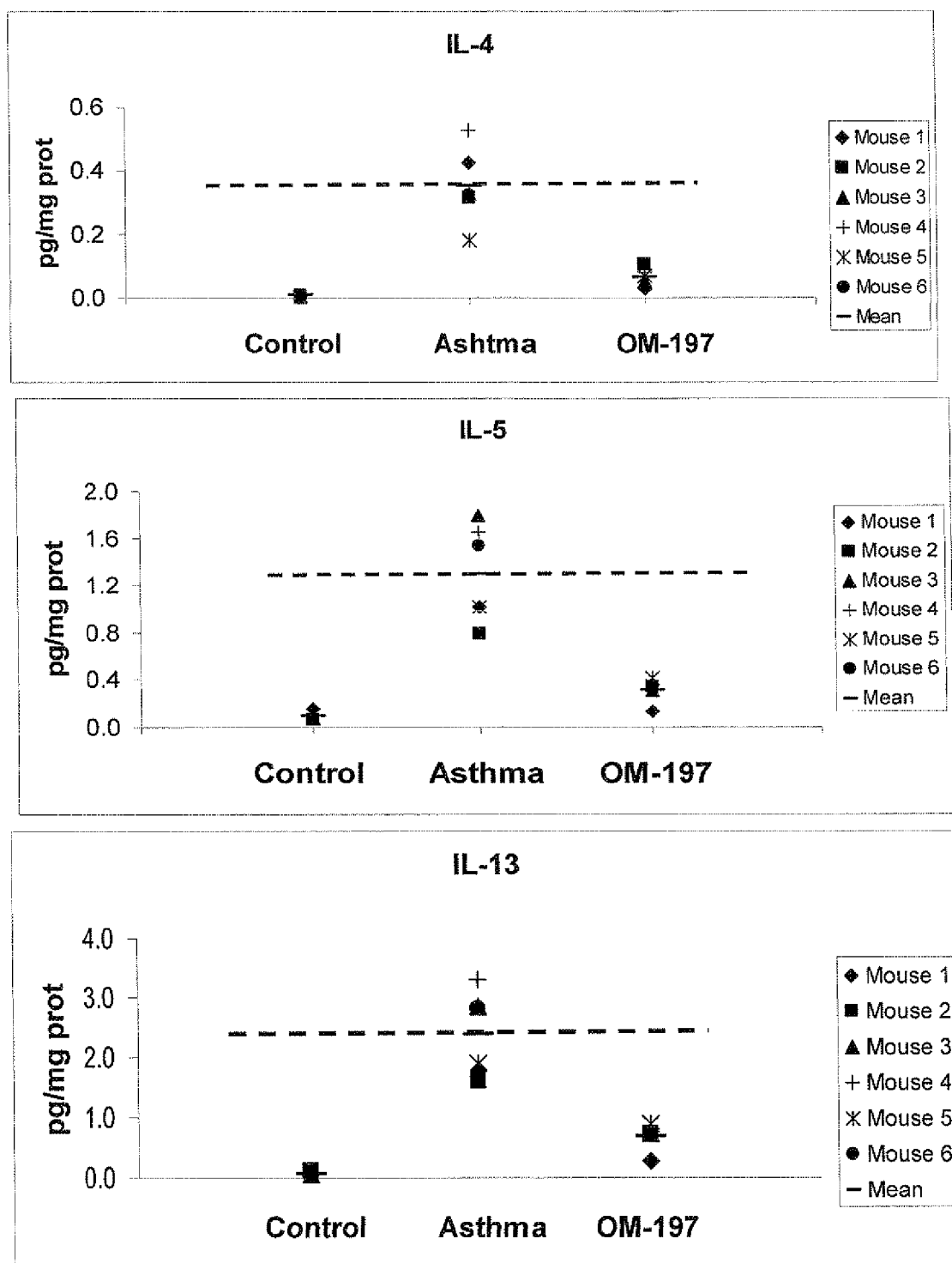

While the amounts of IL-4, IL-13, and IL-5 were under the limit of detection in lungs of LACK-sensitized and PBS-challenged mice (see "Control" in FIG. 7) the amounts of these cytokines increased dramatically upon LACK challenges (see "Asthma" in FIG. 7). In contrast, lungs of LACK-sensitized and challenged mice that have been treated with OM-197-MP-AC contained 5 times less IL-4 ($p=0.0003$) 5 times less IL-5 ($p=0.0003$); and 3.5 times less IL-13 ($p=0.003$) than untreated mice (see "OM-197" in FIG. 7).

Beside IL-4, IL-5, and IL-13, other cytokines were quantified by multiplex analysis using CBA array beads and FACSarray. The main results are reported herebelow. IFN-$\gamma$ was also found to be upregulated in lungs of LACK-sensitized and challenged mice as compared to LACK-sensitized and PBS-challenged mice. Lungs of OM-197-MP-AC-treated mice contained both 2-times less IFN-$\gamma$ than those of untreated mice. KC is the functional homologous chemokine of human IL-8 or CXCL8, and binds to CXCR2 expressed by both neutrophils and eosinophils. Indeed, KC may allow the recruitment of granulocytes to inflamed tissues. While KC was present in very low quantity in lungs of LACK-sensitized and PBS-challenged mice, its expression highly increased upon LACK aerosol challenges. The amount of KC produced in lungs was reduced by half upon treatment with OM-197-MP-AC.

The pro-inflammatory cytokine, IL-6 was found in lungs of LACK-sensitized and PBS-challenged and slightly increased upon LACK aerosols. Lungs of OM-197-MP-AC-treated mice exhibited 1.5-times less IL-6 than those of untreated mice. The chemokine MCP-1 was found to be expressed in lungs of sensitized and PBS-challenged mice and was slightly upregulated upon challenge. Lungs of mice that were treated with OM-197-MP-AC contained 1.8 times less MCP-1 than those of untreated animals.

The amounts of TNF-$\alpha$ in lungs of treated and untreated mice did not yield significant differences.

IL-9 was not detected in any of the samples.

Taken together these data clearly indicate that prophylactic OM-197-MP-AC induces not only a strong decrease of Th2 cytokines that are crucial for inducing allergic airway inflammation, and AHR, but also a decrease of other cytokines and chemokine which contribute to the lung inflammation and to the recruitment of inflammatory effector cells such as eosinophils.

General Conclusion for Example 8 a:

This study clearly demonstrated a protective role of one the molecules of the invention, OM-197-MP-AC, in the development of allergic asthma. Treatments with OM-197-MP-AC starting just before the sensitization phase inhibited the development of AHR, and strongly decreased BAL eosinophilia. In addition, the amounts of total IgE were decreased in the serum of mice that had been treated with OM-197-MP-AC.

The data also show that OM-197-MP-AC treatments impaired mainly the development of cytokines involved in asthma, and the secretion of other inflammatory cytokines. One possible mechanism would be that OM-197-MP-AC might induce a specific immunosuppressive response that would control Th2 development, and subsequent airway inflammation.

Part B) "Therapeutic" Treatment of Asthma
Protocol:

The Main Differences Compared to the Previous (Part a) Protocol are:

Mice were treated with OM-197-MP-AC i.p. only on days 15, 17 and 19 (i.e. at least 1 week after the second sensitization) at the dose of 1 mg/Kg (20 µg per mouse).

The lung cytokines measured by multiplex analysis using FACSArray were IL-4, IL-5, IL-13, IFN-$\gamma$, and IL-10.

Figure 8:
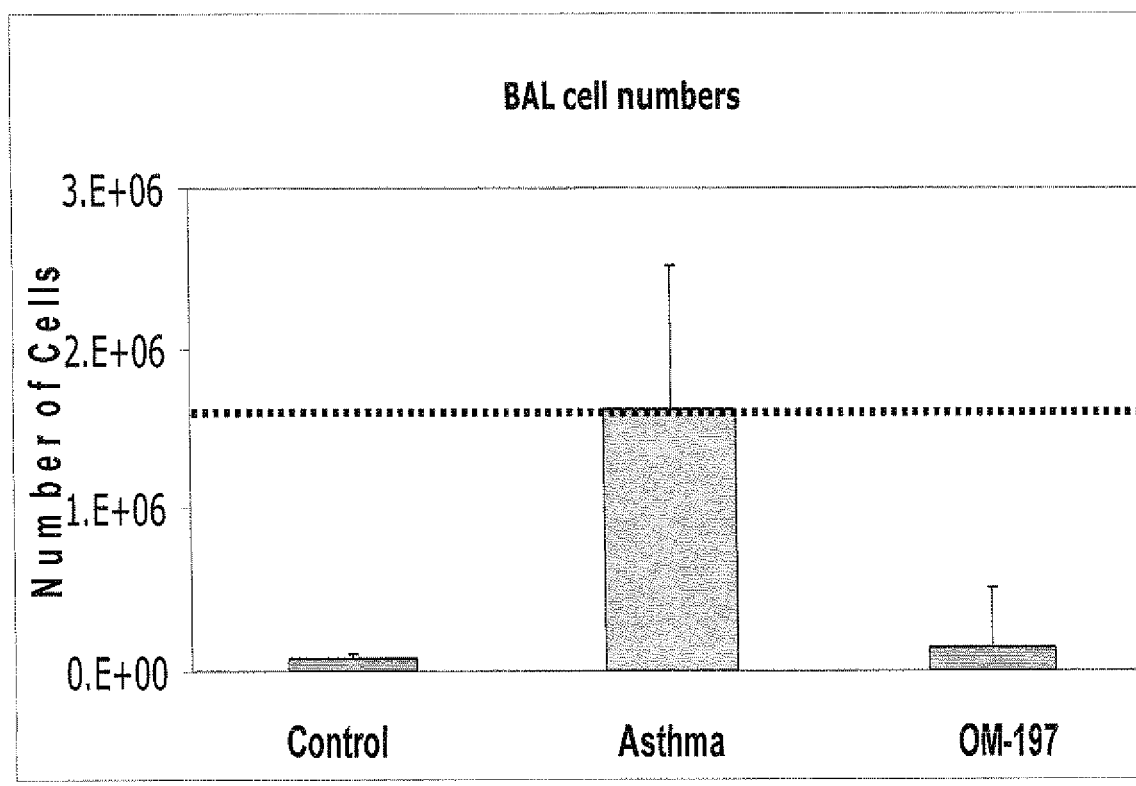

Results:
Total Cell number and eosinophils in BAL:

Two days after the last aerosol, mice were sacrificed and BAL cells harvested. As expected, untreated LACK-sensitized mice exhibited a massive influx of cells in BAL upon LACK challenges (20-fold more cells as compared to PBS-challenged mice) (FIG. 8). Very interestingly, BAL cell recruitment was impaired by 90% upon therapeutic administrations with OM-197-MP-AC ($p<0.01$) (FIG. 9), with 40-45-fold less eosinophils as compared to untreated mice.

Conclusion:

OM-197-MP-AC provided three times therapeutically was able to dramatically decrease pulmonar cellular extravasion and eosinophilia in BAL.

Figure 10:
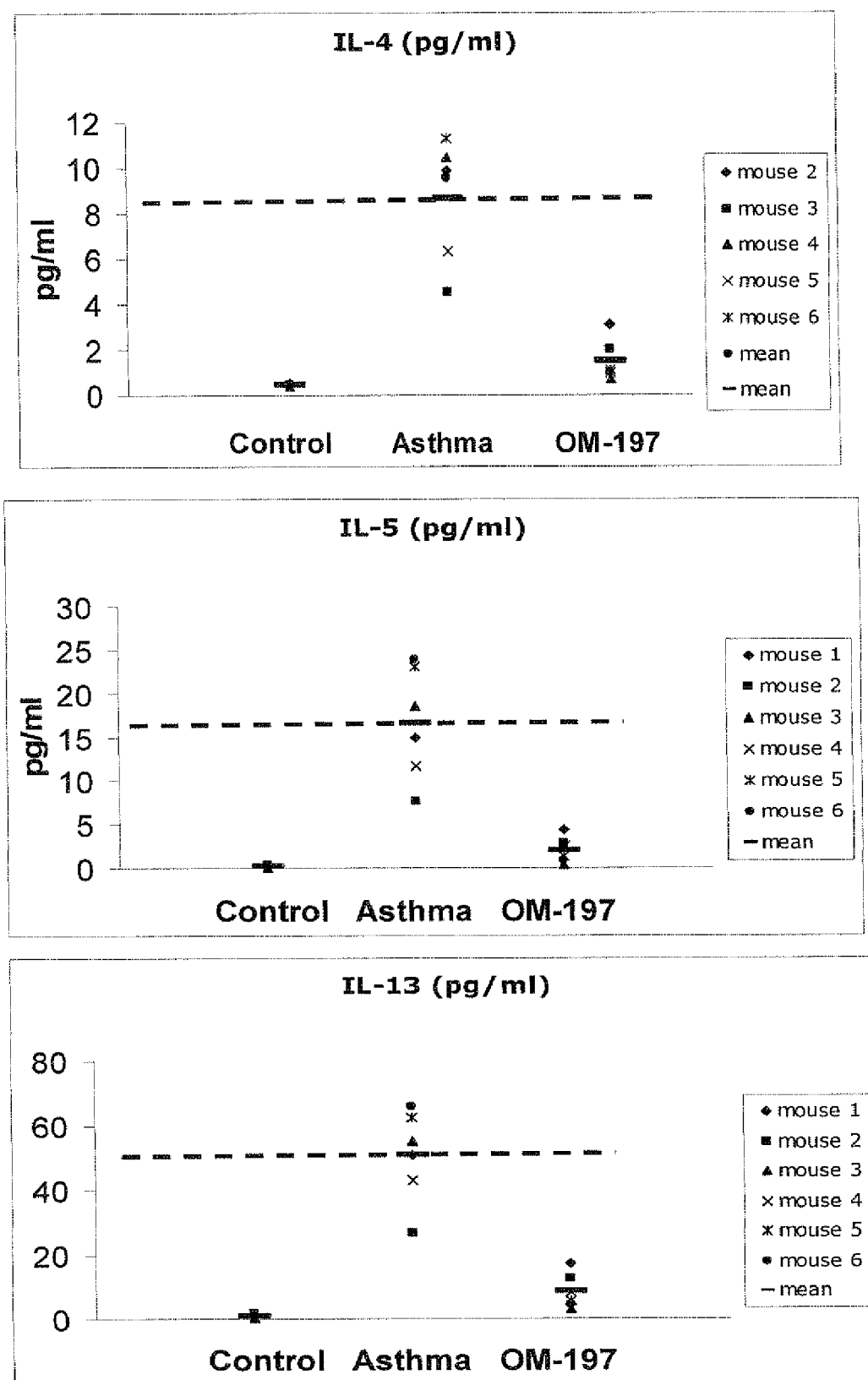

Measurements of Lung Cytokines:

Since airway eosinophilia was so drastically reduced upon therapeutic treatment with OM-197-MP-AC, we sought of analyzing IL-4, IL-5, IL-13, IL-10 and IFN-$\gamma$, lung contents (FIG. 10). Indeed, when compared to lungs of untreated mice, the amounts of the Th2-cytokines: IL-4, IL-5 and IL-13 were strongly reduced in lungs of treated mice. IL-4 levels were reduced by 90%, IL-13 amounts by 85%, and IL-5 amounts by 70% upon treatment with OM-197-MP-AC (from $p<0.00005$ to 0.005).

Conclusion:

Clearly OM-197-MP-AC when provided therapeutically only three times was able to decrease the level of Th2 cytokines. This was not due to a shift towards Th1 cytokine since IFN-γ levels remained low (1.5 to 3 pg/ml) for all mice and were reduced in treated mice. The amounts of IL-10 that is both a Th2 and an immunosuppressive cytokine, were low, and were not significantly increased upon treatment Measurement of IgE Levels:

In order to further characterize the immune status of mice after therapeutic treatment with OM-197-MP-AC, we analyzed LACK-specific IgE in sera of treated mice and in those of untreated mice by ELISA. Whereas LACK-specific IgE levels increased 7-fold upon exposition to LACK aerosols, sera of OM-197-MP-AC-treated mice contained 2-fold less ($p<0.05$) LACK-specific IgE compared to untreated LACK challenged mice.

Conclusion:

Clearly OM-197-MP-AC when provided therapeutically decreased seric LACK-specific IgE levels.

General Conclusion for Example 8b.

We demonstrated here, that the product of the invention, OM-197-MP-AC, when provided therapeutically, clearly decreased eosinophilia, as well as the level of Th2 cytokines such as IL-4, IL-5, and IL-13, and also the level of the allergen-specific IgE General Conclusion for Example 8

Clearly OM-197-MP-AC was active both preventively and therapeutically in vivo in a model of asthma, as judged by its effects on many asthma-relevant read-outs.

Example 9

Effect of OM-197-MP-AC by Other Routes of Administration in the Murine Model of Asthma The results presented in example 8 show that OM-197-MP-AC is effective in the prevention of allergic responses in the murine LACK model of asthma, when administered by the i.p. route. Other ways of administration, more compatible with the human usage, were therefore investigated in this model (intranasal, intragastric, subcutaneous).

Protocol:

43 females BALB/c ByJ mice 6-week old were purchased from the Centre d'Elevage Janvier (CERJ, Le Genest-St-lsle, France). All the mice were sensitised by 2 i.p. injections of 10 μg LACK protein precipitated in 2 mg of Alum (PerBio Science France SAS, Brebières, France) at days 1 and 8 (Julia et al., 2002). OM-197-MP-AC was given from day 0 to day 12 as described below. All the mice were challenged from day 16 to day 20 with either a solution of LACK (0.15%) or with PBS as indicated below.

Experimental groups were the following:
Group A: untreated, LACK-sensitised and PBS-challenged mice (3 mice)
Group B: untreated LACK-sensitised and -challenged mice (7 mice)
Group C: i.p. OM-197-MP-AC-treated, LACK-sensitised and -challenged mice (5 mice)
Group D: i.g. OM-197-MP-AC-treated, LACK-sensitised and -challenged mice (7 mice)
Group E: s.c. OM-197-MP-AC-treated, LACK-sensitised and -challenged mice (7 mice).
Group F: i.n. OM-197-MP-AC-treated, LACK-sensitised and -challenged mice (7 mice)
Group G: aerosols OM-197-MP-AC-treated, LACK-sensitised and -challenged mice (7 mice)

Mice of groups C, D, E, and G were treated on days: 0, 2, 3, 4, 7, 9, 10, 11, whereas mice of group F (intranasal route) were only treated on days 0, 4, 7, and 11.

Mice of groups C and E were treated i.p. and s.c. respectively with 1 mg/Kg (20 μg per mouse) of OM-197-MP-AC.

Mice of group D were treated intragastrically with 50 mg/Kg (1 mg per mouse) of OM-197-MP-AC.

Mice of group F were treated i.n. with 20 μg of OM-197-MP-AC in a volume of 20 μl (OM-197-MP-AC at 2 mg/ml, 10 μl/nostril.)

Mice of group G received aerosols of a solution of OM-197-MP-AC at 0.2% (2 mg/ml) for 10 minutes.

Reagents:
LACK recombinant protein was produced in *E. coli* and purified as described (Mougneau et al., 1995).
OM-197-MP-AC, batch #050323, at the concentration of 2.2 mg/ml, and batch #050322, at the concentration of 2.17 mg/ml were provided by OM PHARMA, and used for oral and all the other administrations, respectively.
Anti-IgE (R35-118) coupled to biotin, was purchased from BD Biosciences (Le Pont de Claix, France). Anti-IgE EM-95 mAbs were a gift from DNAX (Palo Alto, Calif., USA).
Intranasal treatment was performed after light anaesthesia of the mice using Isoflurane (Aerrane, Baxter).

Antibody Titers:

All the mice were bled by heart puncture 2 days after the last aerosol. Total IgE were quantified by ELISA using rat EM-95 anti-IgE mAbs as coating antibody and rat anti-IgE mAbs coupled to biotin as second antibody as described elsewhere (Julia et al., 2002).

Analysis of Bronchoalveolar Lavage (BAL) Cells:

Individual mice were bled and a canula was inserted into their trachea. Lungs were washed 3 times with 1 ml of warmed PBS. Cells were washed with PBS, resuspended in 300 μl, and counted using a Burker-Türk chamber. For differential BAL cell counts, cytospin preparations were made and stained with Wright/Giemsa.

Figure 11:
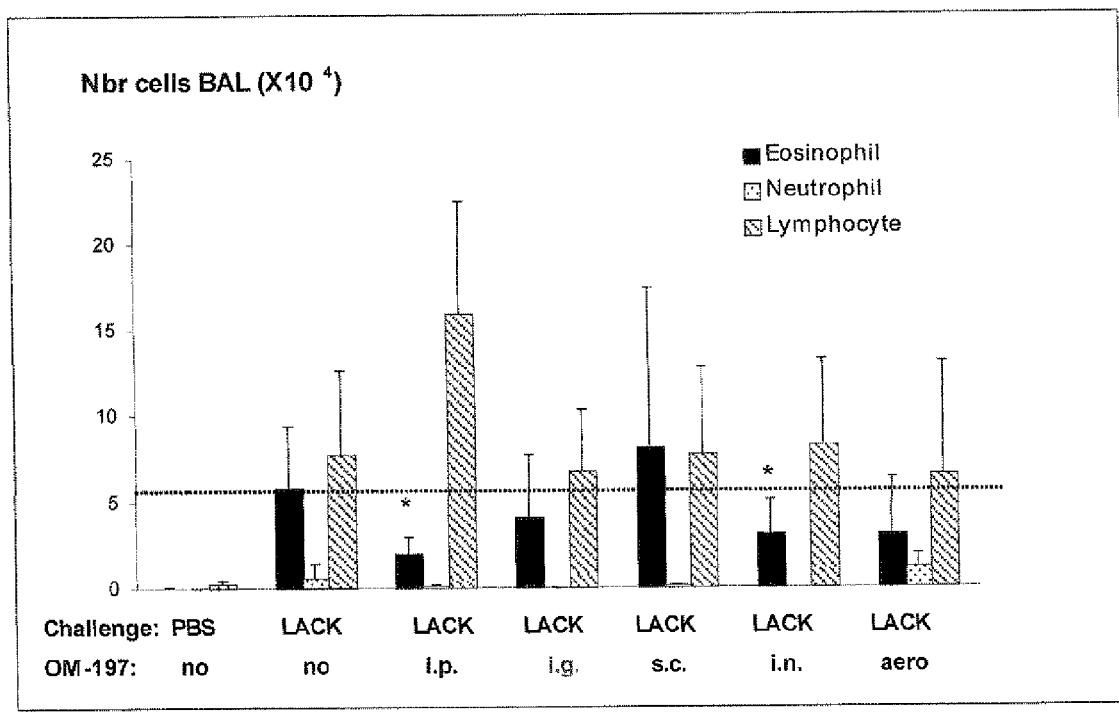

Results:

a) The respective numbers of neutrophils, eosinophils, lymphocytes, and other mononuclear cells were determined by microscopic examination and are reported in FIG. 11 for each route of administration tested.

As the inventors had previously reported in example 8, mice treated i.p. with OM-197-MP-AC exhibited both reduced percentage and reduced numbers of eosinophils in BAL. However, BAL cell contents of mice treated s.c. and i.g with OM-197-MP-AC did not yield differences with those of untreated mice. In contrast, both eosinophil frequencies (not shown) and numbers (FIG. 11) were reduced by half in BAL of mice that had received i.n. OM-197-MP-AC. In addition, mice treated with OM-197-MP-AC aerosols exhibited the same tendency as i.n. treated animals.

Figure 12:
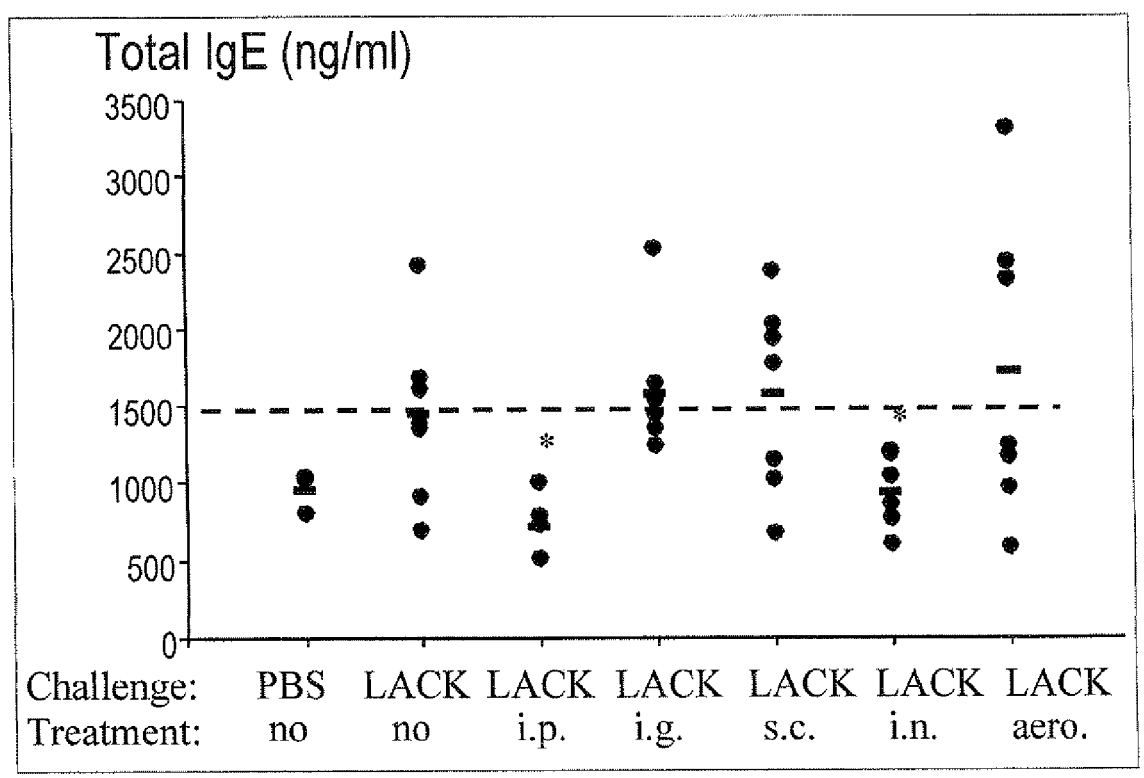

Conclusion:

At least OM-197-MP-AC was significantly efficient in both the i.p. and the intranasal routes to significantly diminish in this model the number of eosinophils in the bronchoalveolar lavages of mice sensitized to an allergen.

b) Then, plasmatic IgE levels were measured as described in the method section. In agreement to our previous data (example 8), we found that mice that had been treated i.p. with OM-197-MP-AC exhibited reduced amounts of total IgE (FIG. 12). In addition, mice that had received i.n.

injections of OM-197-MP-AC also exhibited reduced titers of total serum IgE. In contrast, mice treated i.g., s.c. or with aerosols presented similar amounts of total serum IgE as compared to untreated mice.

Conclusion:

OM-197-MP-AC administered either by the i.p. or by the intranasal route decreased significantly total IgE levels in this model of asthma.

Example 10

Increased Effect of Formulated OM-197-MP-AC by the Oral Route of Administration in the Murine Model of Asthma The results presented in example 9 show that OM-197-MP-AC is ineffective in the prevention of allergic responses in the murine LACK model of asthma, when administered unformulated by the oral route. An assay of formulation in order to increase the activity of OM-197-MP-AC by the oral route was therefore investigated in this model. Therefore in this study, we investigated whether the triacylated OM PHARMA compound OM-197-MP-AC would protect mice against allergic airway inflammation when provided as a gastro-intestinal resistant formulation (OM-197-MP-AC with Lutrol® F 127, also known as poloxamer 407).

Protocol:

The OM-197-MP-AC/Lutrol® F 127 formulation was prepared by mixing 12.875 ml of a solution of OM-197-MP-AC at 4.35 mg/ml and 5.6 mL of Lutrol F127 at 50 mg/ml. The administered volume was 330 μl.

Reagents and Equipment
  Saline solution were given as control aerosols
  Recombinant LACK protein was produced in *E. coli*, and purified onto a Ni-NTA affinity column
  Aluminium hydroxide (Alum) was purchased from Pierce
  The cytocentrifuge used was a Cytospin 4 (Thermo-Shandon, Cheschire, U.K.), cytoslides were purchased from Thermo-Shandon and Wright and Giemsa stains from Sigma.
  Aerosols were given using an ultra-son nebulizer Ultramed (Medicalia, Forenze, Italy)
  CBA beads array IL-4 were purchased from BD Biosciences.
  The flow cytometer FACSarray has been purchased from BD Biosciences.

Animals:
  6 weeks old female BALB/c ByJ mice were purchased from The Centre d'Elevage Janvier, France, and were kept under specific-pathogen free conditions in the animal facility. They were fed with a standard diet provided by Safe (Augy, France).

Protocol:
  15 BAL/c mice (including the mice for the control groups A and B, shown also in the examples 8 and 9) were used for this experiment.
  A: untreated LACK-sensitized and saline-challenged mice (3 mice)
  B: untreated LACK-sensitized and challenged mice (6 mice)
Prophylactic Treatment
  F: OM-197-MP-AC (oral)-treated LACK-sensitized and challenged mice (6 mice)
  Mice of group F were treated orally on days 0, 2, 3, 4, 7, 9, 10 11, and 12 with 1 mg of formulated OM 197 MP AC.
  On day 1 and day 8, mice were sensitized i.p. with LACK/Alum. From day 16 to day 20, all the groups except group A mice were challenged with aerosols of a solution of LACK (0.15%). Group A received a saline solution (NaCl 0.9%) for 40 minutes instead.
  At day 22, all the mice will be sacrificed. For all the animals, BAL, and lungs without peri-bronchial lymph nodes were harvested.
  BAL cells will be counted and cell contents will be analyzed after microscopic examination of cytospins following wright/giemsa staining. In addition, lungs of each group were harvested and frozen in liquid nitrogen for further cytokine content analysis. To investigate cytokine content, protein extracts will be prepared from lungs of LACK-sensitized and PBS-challenged mice (group A), LACK-sensitized and challenged mice (group B), and formulated OM-197-MP-AC-treated wt mice (group F). IL-4 amount was analyzed by multiplex analysis using FACSArray.

Figure 13:
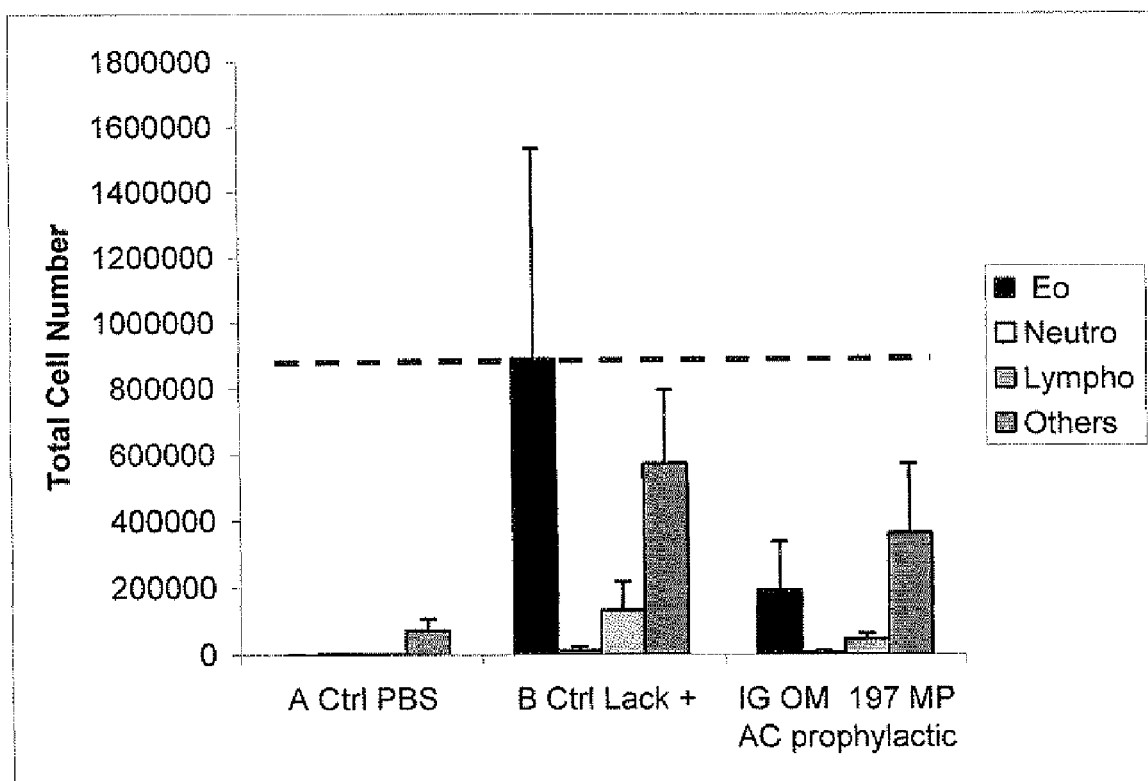

Results:

The respective numbers of neutrophils, eosinophils, lymphocytes, and other mononuclear cells were determined by microscopic examination and are reported in FIG. 13.

In contrast to the results reported in example 8 (and FIG. 11) were BAL cell contents of mice that have been treated i.g with OM-197-MP-AC (unformulated), when OM-197-MP-AC was formulated with Lutrol, the number of neutrophils, eosinophils ($p<0.05$), lymphocytes, and other mononuclear cells were reduced by half in BAL of mice that had received formulated OM-197-MP-AC (see FIG. 13).

Moreover, IL-4 amounts were analyzed in lungs of treated and untreated mice. Whereas IL-4 lung contents were very low to undetectable in PBS-challenged animals, IL-4 amounts increased 20-fold in LACK-challenged untreated control mice. Upon oral treatment with formulated OM-197-MP-AC (see FIG. 14), the amounts of IL-4 in lungs decreased by 75% ($p<0.01$)

Conclusion:

When adequately formulated, oral OM-197-MP-AC was able to significantly diminish in this model the number of eosinophils in the bronchoalveolar ravages of mice sensitized to an allergen. This decrease was correlated with a decrease in IL-4.

Example 11

Effect of OM-197-MP-AC on Non Obese Diabetic (NOD) Mice

So far, we provided examples of the in vivo efficacy of OM-197-MP-AC only in a murine model of asthma. In this example, we will provide some evidence that OM-197-MP-AC is also active in another inflammatory pathology: diabetes.

Protocol:

We have previously shown that OM-197-MP-AC and other triacylated molecules decrease airway inflammation in asthmatic animals.

In this study, we investigated whether OM-197-MP-AC would be able to induce protection, in another model of murine inflammatory disease: the NOD diabetes model (Non Obese Diabetic).

Group of 10 female 6-week old NOD mice were treated during 10 weeks with either 0.01, 0.1, and 1 mg/kg of OM-197-MP-AC. A group of 6 female MOD mice receiving 200 μl PBS i.p. 3 times a week was used as control.

In this series of experiments, the treatment was continued until the mice have reached 16 weeks of age. This is the point in time when control animals start developing overt diabetes.

Results in terms of diabetes incidence were compared to those obtained in control animals. Diabetes was checked once a week by glucosuria testing, using test strips (Glukotest®, Roche, France), twice a week when diabetes appeared. Diabetes was confirmed by evaluating glycemia (>3 mg/ml) with test strips (Glucotrend®).

The occurrence of diabetes in the different experimental groups is plotted (see FIG. 15) using the Kaplan-Meier method, i.e. non parametric cumulative survival plot. The statistical comparison between the curves is performed using the logrank (Mantel-Cox) test which provided the corresponding $\chi 2$ values. OM-197-MP-AC at the dose of 1 mg/kg was significantly active (p=0.0321), and at the dose of 0.1 mg/kg the compound of the invention exhibited a positive trend (p=0.0543).

In another experiment using a dose of OM-197-MP-AC of 0.3 mg/kg, the results obtained at week 27 show a significant p value of 0.0362. At week 27, 82% of the animals were found diabetic in the control group and only 27% in the OM-197-MP-AC treated group (0.3 mg/kg) exhibited the disease.

Example 13

Toxicology: LAL Endotoxicity

Endotoxicity was determined first for OM-197-MP-AC and for OM-294-DP by the *Limulus* Amoebocyte Lysate chromogenic test (Chromogenic—LAL of Bio-Whittaker, kit n°50-650U).
Protocol:

This test is based on activation by lipopolysaccharide (LPS) or products of comparable structure, by an enzymatic cascade present in the LAL. This enzymatic activation is demonstrated by the splitting of a chromogen linked to a peptide by a protease. The enzymatic reaction is carried out at 37° C. and the formation of the chromogen over time is measured at 405 nm. The time necessary to reach 0.2 units of D.O. is recorded and the endotoxic activity calculated in relation to a LPS standard (standard curve). The results are expressed in EU (Endotoxin Unit) in relation to a standardized preparation of *E. coli* LPS (1 EU corresponds to 0.08 ng equivalent LPS).
Results:

Both OM-197-MP-AC and OM-294-DP showed very little or no *Limulus* activity in the chromogenic LAL assay.
Conclusion:

OM-197-MP-AC and OM-294-DP are very weakly endotoxic (at least $10^6$ fold decrease) when compared to LPS.

Example 14

Toxicology: Pyrogenicity in the Rabbit

Finally, OM-197-MP-AC and OM-294-DP were tested for their potential pyrogenicity in the rabbit.
Protocol:

3 New Zealand white rabbits/group were injected i.v. with either OM-197-MP-AC or OM-294-DP at different doses (according to the European Pharmacopoeia 2001, Method 2.6.8).
Products: OM-197-MP-AC at 0.0009, 0.009, 0.09, 0.9 mg/kg, and OM-294-DP at 0.001, 0.01, 0.1, and 1 mg/kg.
Animals: Readout: temperature increase
Results:

Both compounds were considered not pyrogenic in vivo, since the pyrogenic threshold of OM-197-MP-AC was not reached at the highest dose tested (0.9 mg/kg), and the pyrogenicity of OM-294-DP was only reached between 0.01 and 0.1 mg/kg.

REFERENCES

Byl, B., Libin, M., Bauer, J., Martin, O. R., De Wit, D., Davies, G., Goldman, M., and Willems, F. (2003). OM197-MP-AC induces the maturation of human dendritic cells and promotes a primary T cell response. Int Immunopharmacol 3, 417-425.

Julia, V., Hessel, E. M., Malherbe, L., Glaichenhaus, N., O'Garra, A., and Coffman, R. L. (2002). A restricted subset of dendritic cells captures airborne antigens and remains able to activate specific T cells long after antigen exposure. Immunity 16, 271-283.

Mougneau, E., Altare, F., Wakil, A. E., Zheng, S., Copolla, T., Wang, Z.-E., Waldmann, R., Locksley, R., and Glaichenhaus, N. (1995). Expression cloning of a *Leishmania major* protective T cell antigen. Science 268, 563-566.

Veran, J., Mohty, M., Gaugler, B., Chiavaroli, C., and Olive, D. (2004). OM-197-MP-AC adjuvant properties: the in vitro maturation of normal and leukemic dendritic cells in a serum-free culture model. Immunobiology 209, 67-77.

FIGURE LEGENDS

FIG. 1: IL-12 (left panels) and IL-10 (right panels) secretion by murine DC stimulated by LPS (1 µg/ml) alone, or first during 90 minutes with the indicated concentrations (in µg/ml) of OM-197-MP-AC (A) or 294-DP (B), and then by LPS (1 µg/ml) for 20 additional hours. The supernatants were collected from the DC cultures and analyzed by ELISA for the presence of IL-12 and IL-10.

FIG. 2: TNF-α secretion by murine DC stimulated by LPS (1 µg/ml) alone, or first during 90 minutes with the indicated concentrations (in µg/ml) of 294-DP (294), or of OM-197-MP-AC (197), and then by LPS (1 µg/ml) for 20 additional hours. The supernatants were collected from the DC cultures and analyzed by ELISA for the presence of TNF-α.

FIG. 3: Effect of increasing doses of the four compounds tested (OM-197-MP-AC, n=5; OM-197-MC-HD, n=5; OM-294-BA-MP, n=7; OM-197-MP-HD, n=3) on IFN-γ and IL-13 production of human CD4$^+$ T cells following a polyclonal activation. Results are expressed as the median (±p25/p75) of n independent experiments and show the percentage (%) proliferation or cytokine production of treated cells versus untreated cells (considered as 100%, see dotted line). The statistical analysis was performed using a nonparametric unpaired Mann-Whitney t test (2-tailed).

FIG. 4: AHR by whole-body plethysmography (Emka) in response to increasing concentrations (6-25 mg/ml) of inhaled methacholine one day after the last antigen challenge. The animals were treated as described in the protocol section. Results (mean "enhanced pause value"+/−SEM) are shown for saline-challenged animals (as the negative control group, n=4), untreated LACK-challenged animals (as the positive control group, n=8), and OM-197-MP-AC-treated LACK challenged mice (n=8).

FIG. 5: Percentage of eosinophils in bronchoalveolar lavages analyzed by microscopic examination of cytospin preparations stained with Wright/Giemsa coloration. The groups studied are the same as those used in FIG. 4. The dotted line indicates throughout the graph the value obtained in untreated asthmatic animals.

FIG. 6: All the mice were treated as described in the protocol section, and were bled by heart puncture one day after the last aerosol. Total IgE were quantified by ELISA using rat EM-95 anti-IgE mAbs as coating antibody and rat anti-IgE mAbs coupled to biotin as second antibody as described (Julia et al., 2002). Each point corresponds to a single animal. The groups studied are the same as those used in FIGS. 4 and 5.

FIG. 7: Protein extracts (400 µl) were prepared from left lungs of LACK-sensitized and PBS-challenged wt mice (Control), LACK-sensitized and challenged wt mice (Asthma), OM-197-MP-AC-treated wt mice (OM-197). IL-4, IL-5 and IL-13 contents were analyzed by multiplex analysis using FACSArray. Results are given in pg/ml. The dotted lines indicate throughout the graphs the values obtained in untreated asthmatic animals.

FIG. 8: Mice were therapeutically treated three times as described in the method section, lavages were performed in individual mice bled with a canula inserted into their trachea. Lungs were washed 3 times with 1 ml of warmed PBS. Cells were washed with PBS, resuspended in 300 µl, and counted using a Burker-Türk chamber. For differential BAL cell counts, cytospin preparations were made and stained with Wright/Giemsa coloration. The groups tested were: LACK-sensitized and PBS-challenged wt mice (Control), LACK-sensitized and challenged wt mice (Asthma), and OM-197-MP-AC-treated wt mice (OM-197). The total cell number in BAL was determined by microscopic examination of cytospin preparations stained with Wright/Giemsa coloration. The dotted line indicates throughout the graph the value obtained in untreated asthmatic animals.

Figure 9:
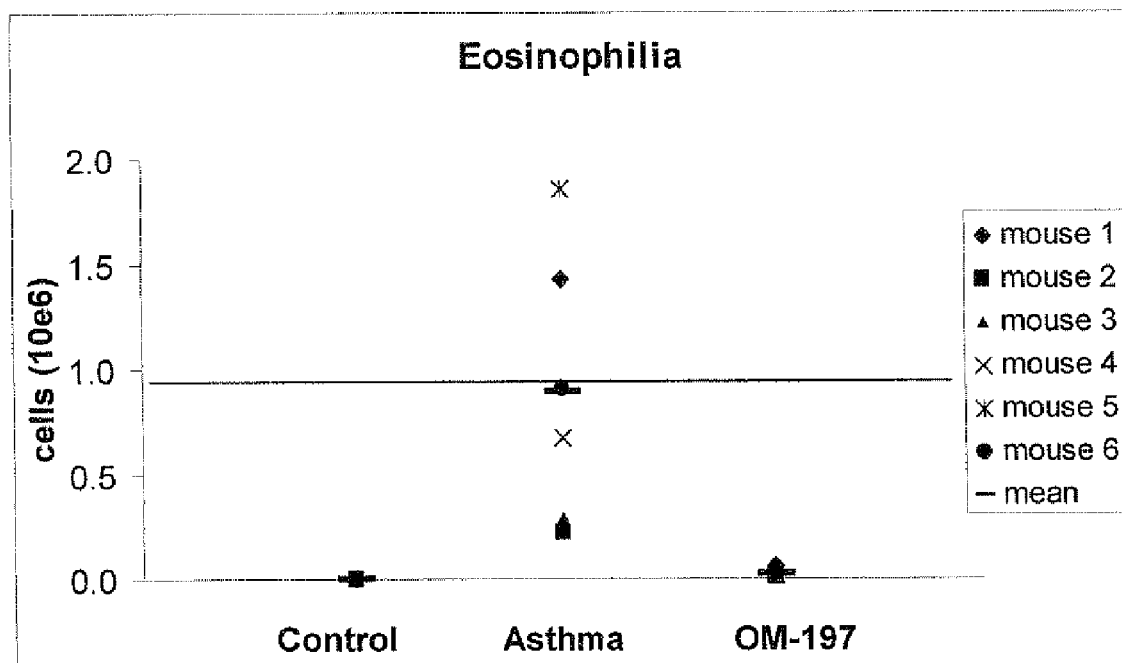

FIG. 9: Percentage of eosinophils in BAL analyzed by microscopic examination of cytospin preparations stained with Wright/Giemsa coloration. Mice were therapeutically treated three times as described in the method section, cells from BAL were harvested as explained in FIG. 8. The (therapeutic) groups studied are the same as those used in FIG. 8. The dotted line indicates throughout the graph the value obtained in untreated asthmatic animals.

FIG. 10: To analyze lung cytokine contents, lungs were harvested and left lungs were used to prepare protein extracts. 400 µl were recovered for each left lung. Cytokines were measured by multiplex analysis using FACSArray, and results are given in pg/ml. The (therapeutic) groups studied are the same as those used in FIGS. 8 and 9. The dotted lines indicate throughout the graphs the values obtained in untreated asthmatic animals.

FIG. 11: Number of eosinophils, neutrophils, and lymphocytes in murine BAL. Cells were obtained and washed as described in the protocol section. For differential BAL cell counts, cytospin preparations were made and stained with Wright/Giemsa. At least 400 cells were scored for each slide, and the numbers of eosinophils, neutrophils, and lymphocytes were determined by microscopic examination. The dotted line indicates throughout the graph the value obtained in untreated asthmatic animals.

FIG. 12: Measurement of Allergen-specific IgE in murine sera were bled by heart puncture two days after the last aerosol, and sera were prepared. LACK-specific IgE were measured by ELISA. Results (ng/ml) from individual mice are reported, the mean value in each group is represented by a bar. *=P<0.05. The dotted line indicates throughout the graph the value obtained in untreated asthmatic animals.

FIG. 13: Number of eosinophils, neutrophils, and lymphocytes in murine BAL. Cells were obtained and washed as described in the protocol section. For differential BAL cell counts, cytospin preparations were made and stained with Wright/Giemsa. At least 400 cells were scored for each slide, and the numbers of eosinophils, neutrophils, lymphocytes, and other cells (macrophages, dendritic cells, and pnuemocytes) were determined by microscopic examination. The 3 groups tested were described in the protocol section of example 10. The dotted line indicates throughout the graph the value obtained in untreated asthmatic animals.

Figure 14:
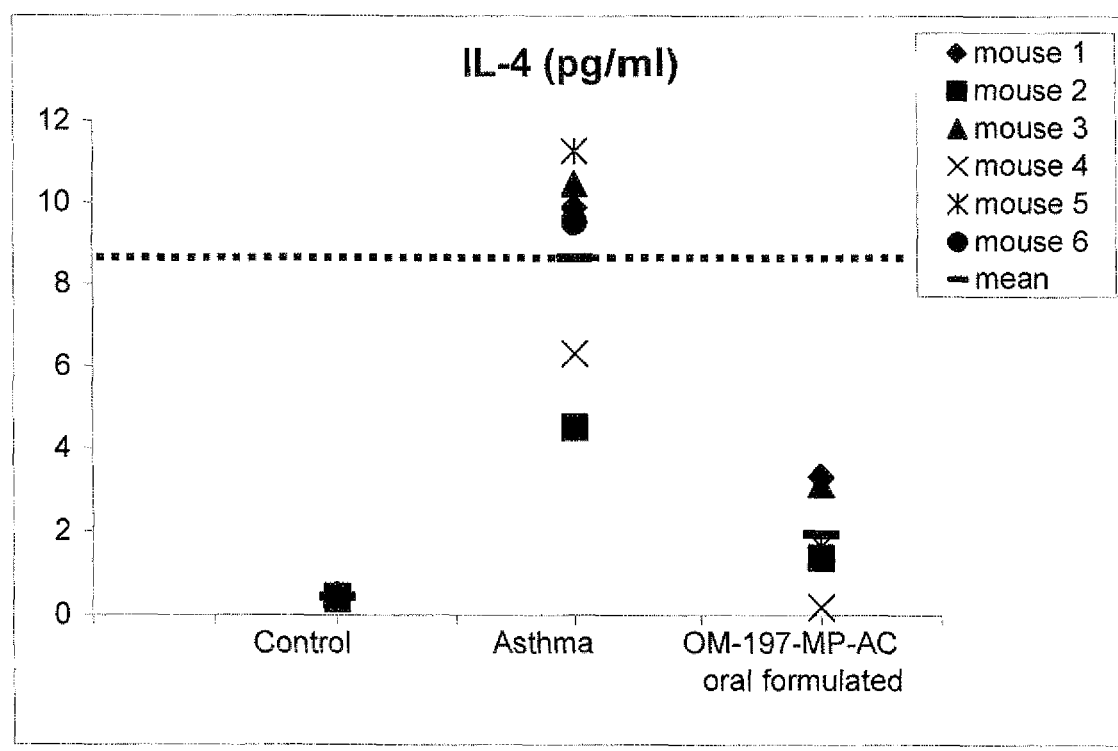

FIG. 14: To analyze lung cytokine contents, lungs were harvested and left lungs were used to prepare protein extracts. 400 µl were recovered for each left lung. IL-4 was measured by FACSArray, and results are given in pg/ml The 3 groups tested were described in the protocol section of example 10. The dotted line indicates throughout the graph the value obtained in untreated asthmatic animals.

Figure 15:
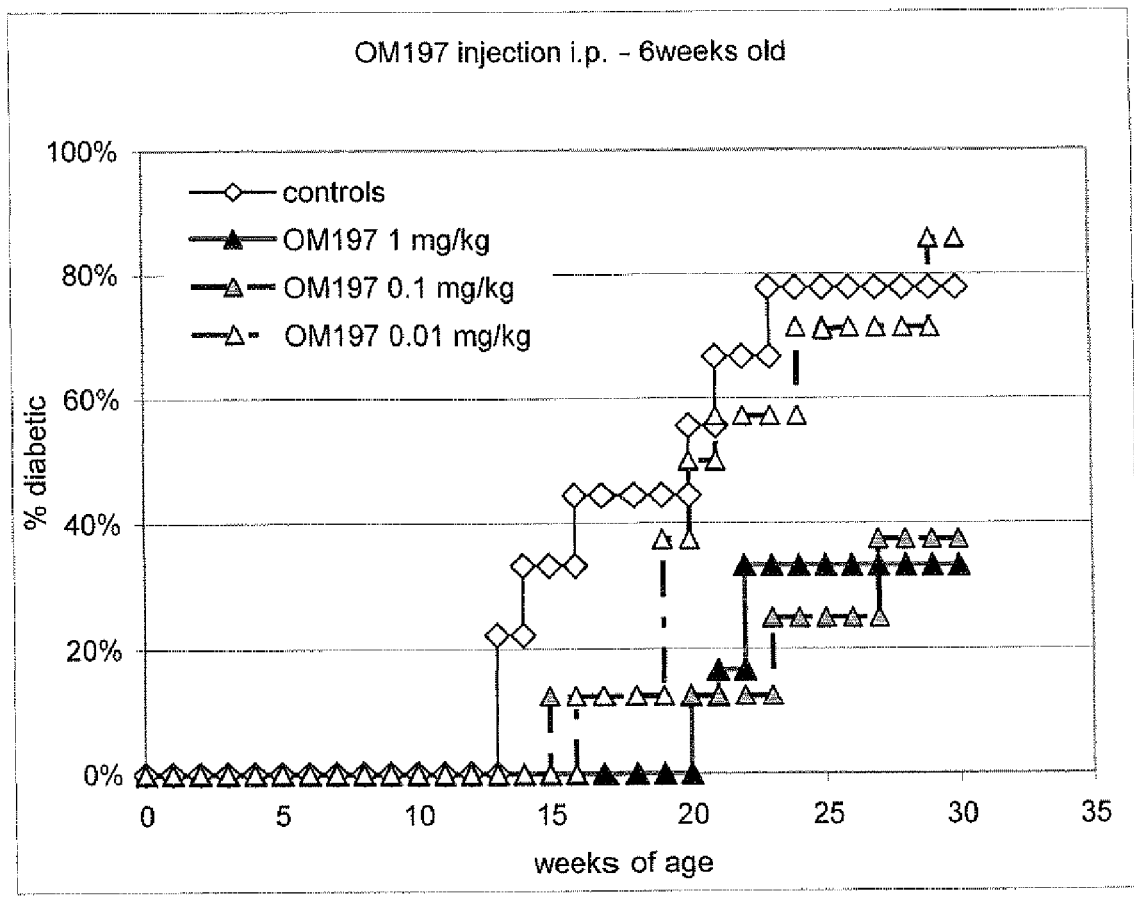

FIG. 15: Occurrence of diabetes in NOD mice. Mice were treated i.p. with either PBS (6 animals), or the 3 indicated doses of OM-197-MP-AC (3 groups of 10 animals). Diabetes was checked once a week by glucosuria testing (Glukotest), and twice a week when diabetes appeared. Diabetes was confirmed by evaluating glycemia (>3 mg/ml) with test strips (Glucotrend®). The occurrence of diabetes in the different experimental groups is plotted (see FIG. 15) using the Kaplan-Meier method, i.e. non parametric cumulative survival plot. The statistical comparison between the curves is performed using the logrank (Mantel-Cox) test which provided the corresponding $\chi 2$ values: OM-197-MP-AC 1 mg/kg p=0.321; 0.1 mg/kg 0.0543.

The invention claimed is:
1. A method for treating warm-blooded animals, including humans, suffering from asthma or allergic rhinitis, comprising the administration to a patient in need thereof of an appropriate amount of a pharmaceutical composition comprising at least one immunomodulatory compound of the following general formula (I):

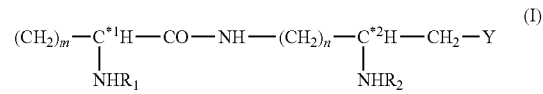

(I)

Wherein:
m and n, independently from each other, are an integer ranging from 1 to 4,
X and Y each designate a group either in neutral or charged state, selected from the following groups:
  carboxyl —COOH,
  dihydroxyphosphoryloxy —O—P(O) (OH)$_2$,
  hydroxysulfonyloxy —O—SO$_2$(OH),
  amino —NH$_2$,
  hydroxyl —OH,
  [amino(C$_1$-C$_{10}$)alkyl]aminocarbonyl —CONH (CH$_2$)$_{n1}$—NH$_2$, with n$_1$ being an integer from 1 to 10,
  [dicarboxy(C$_1$-C$_5$)alkyl]aminocarbonyl —CO—NH—CH(COOH)—(CH$_2$)$_{n1}$—COOH, with n$_1$ being an integer from 1 to 5,
  {carboxy[amino(C$_1$-C$_5$)alkyl]}aminocarbonyl —CO—NH—CH(COOH)—(CH$_2$)$_{n1}$—NH$_2$, with n$_1$ being an integer from 1 to 5,
  amino(C$_1$-C$_{15}$)alkanoyloxy —O—CO—(CH$_2$)$_{n1}$—NH$_2$, with n$_1$ being an integer from 1 to 15,
  dihydroxy (C$_1$-C$_{10}$) alkanoyloxy —O—CO—(CH$_2$)$_{n1}$—CHOH—CH$_2$OH, with n$_1$ being an integer from 1 to 10,
  hydroxy(C$_1$-C$_{10}$)alkanoyloxy —O—CO—(CH$_2$)$_{n1}$—OH, with n$_1$ being an integer from 1 to 10,
  carboxy(C$_1$-C$_{10}$)alkanoyloxy —O—CO—(CH$_2$)$_{n1}$—COOH, with n$_1$ being an integer from 1 to 10, oxo($C_1$-$C_5$)alkanoyloxy —O—CO—$(CH_2)_{n1}$—CHO, with $n_1$ being an integer from 1 to 5,

[carboxy($C_1$-$C_{10}$)alkanoyl]amino($C_1$-$C_{15}$)alkanoyloxy —O—CO—$(CH_2)_{n1}$—NH—CO—$(CH_2)_{n2}$-COOH, with $n_1$ being an integer from 1 to 10, and $n_2$ being an integer from 1 to 15, $R_1$ and $R_2$ each designate an acyl group derived from a saturated or unsaturated, straight-or branched-chain carboxylic acid having from 2 to 18 carbon atoms, which is unsubstituted or bears one to three substituents selected among hydroxyl, dihydroxyphosphoryloxy, alkyl of 2 to 18 carbon atoms, alkoxy of 2 to 18 carbon atoms, acyloxy of 2 to 18 carbon atoms in the acyl moiety, amino, acylamino, $C^{*1}$ and $C^{*2}$, independently from each other being asymmetric carbons in configuration R, S, or in the racemic form RS, or a pharmaceutically acceptable salt or solvate thereof, optionally in conjugation or admixture with an inert non-toxic pharmaceutically acceptable diluent or carrier.

2. A method according to claim 1, wherein:
X is selected from the following groups:
carboxyl —COOH,
dihydroxyphosphoryloxy —O—P(O)(OH)$_2$,
hydroxysulfonyloxy —O—SO$_2$(OH),
amino —NH$_2$,
[amino($C_1$-$C_{10}$)alkyl]aminocarbonyl —CONH—$(CH_2)_{n1}$—NH$_2$, with $n_1$ being an integer from 1 to 10,
[dicarboxy($C_1$-$C_5$)alkyl]aminocarbonyl —CO—NH—CH(COOH)—$(CH_2)_{n1}$—COOH, with $n_1$ being an integer from 1 to 5,
{carboxy[amino($C_1$-$C_5$)alkyl]}aminocarbonyl —CO—NH—CH(COOH)—$(CH_2)_{n1}$—NH$_2$, with $n_1$ being an integer from 1 to 5,
amino($C_1$-$C_{15}$)alkanoyloxy —O—CO—$(CH_2)_{n1}$—NH$_2$, with $n_1$ being an integer from 1 to 15,
and Y is selected from the following groups:
dihydroxyphosphoryloxy —O—P(O)(OH)$_2$,
hydroxysulfonyloxy —SO$_2$(OH),
amino —NH$_2$,
hydroxyl —OH,
amino($C_1$-$C_{15}$alkanoyloxy —O—CO—$(CH_2)_{n1}$—NH$_2$, with $n_1$ being an integer from 1 to 15,
dihydroxy ($C_1$-$C_{10}$) alkanoyloxy —O—CO—$(CH_2)_{n1}$—CHOH—CH$_2$OH, with $n_1$ being an integer from 1 to 10,
hydroxy($C_1$-$C_{10}$alkanoyloxy —O—CO—$(CH_2)_{n1}$—OH, with $n_1$ being an integer from 1 to 10,
carboxy($C_1$-$C_5$alkanoyloxy —O—CO—$(CH_2)_{n1}$—COOH, with $n_1$ being an integer from 1 to 10,
oxo($C_1$-$C_5$)alkanoyloxy —O—CO—$(CH_2)_{n1}$—CHO, with $n_1$ being an integer from 1 to 5,
[carboxy($C_{1-C10}$)alkanoyl]amino($C_1$-$C_{15}$)alkanoyloxy —O—CO—$(CH_2)_{n1}$—NH—CO—$(CH_2)_{n2}$—COOH, with $n_1$ being an integer from 1 to 10, and $n_2$ being an integer from 1 to 15.

3. A method according to claim 1, wherein:
X is selected from the following groups:
carboxyl —COOH,
dihydroxyphosphoryloxy —O—P(O)(OH)$_2$,
hydroxysulfonyloxy —O—SO$_2$(OH),
amino —NH$_2$,
[amino($C_1$-$C_6$)alkyl]aminocarbonyl —CONH—$(CH_2)_{n1}$—NH$_2$, with $n_1$ being an integer from 1 to 6,
[dicarboxy($C_1$-$C_5$)alkyl]aminocarbonyl —CO—NH—CH(COOH)—$(CH_2)_{n1}$—COOH, with $n_1$ being an integer from 1 to 5,
{carboxy[amino($C_1$-$C_5$)alkyl]}aminocarbonyl —CO—NH—CH(COOH) —$(CH_2)_{n1}$—NH$_2$, with $n_1$ being an integer from 1 to 5,
amino($C_2$-$C_{12}$)alkanoyloxy —O—CO—$(CH_2)_{n1}$—NH$_2$, with $n_1$ being an integer from 2 to 12,
and Y is selected from the following groups:
dihydroxyphosphoryloxy —O—P(O)(OH)$_2$,
hydroxysulfonyloxy —O—SO$_2$(OH),
amino —NH$_2$,
hydroxyl —OH,
amino($C_2$-$C_{12}$)alkanoyloxy —O—CO—$(CH_2)_{n1}$—NH$_2$, with $n_1$ being an integer from 2 to 12,
dihydroxy ($C_3$-$C_7$) alkanoyloxy —O—CO—$(CH_2)_{n1}$—CHOH—CH$_2$OH, with $n_1$ being an integer from 3 to 7,
hydroxy($C_2$-$C_6$)alkanoyloxy —O—CO—$(CH_2)_{n1}$—OH, with $n_1$ being an integer from 2 to 6,
carboxy($C_3$-$C_6$)alkanoyloxy —O—CO—$(CH_2)_{n1}$—COOH, with $n_1$ being an integer from 3 to 6,
oxo($C_2$-$C_5$)alkanoyloxy —O—CO—$(CH_2)_{n1}$—CHO, with $n_1$ being an integer from 2 to 5,
[carboxy($C_3$-$C_6$)alkanoyl]amino($C_2$-$C_{12}$)alkanoyloxy —O—CO—$(CH_2)_{n1}$—NH—CO—$(CH_2)_{n2}$—COOH, with $n_1$ being an integer from 3 to 6, and $n_2$ being an integer from 2 to 12.

4. A method according to claim 1, wherein:
X is selected from the following groups:
—COOH,
—O—P(O)(OH)$_2$,
—O—SO$_2$(OH),
—NH$_2$,
—CO—NH—$(CH_2)_3$—NH$_2$, or —CONH—$(CH_2)_6$—NH$_2$,
—CO—NH—CH(COOH)—CH$_2$—COOH,
—CO—NH—CH(COOH)—$(CH_2)_4$—NH$_2$,
—O—CO—$(CH_2)_5$—NH$_2$,
and Y is selected from the following groups:
—O—P(O)(OH)$_2$,
—O—SO$_2$(OH),
—NH$_2$,
—OH,
—O—CO—CH$_2$—NH$_2$ (2-aminoethanoyloxy),
—O—CO—$(CH_2)_2$—NH$_2$ (3-aminopropanoyloxy),
—O—CO—$(CH_2)_5$—NH$_2$ (6-aminohexanoyloxy),
or —O—CO—$(CH_2)_{11}$—NH$_2$ (12-aminododecanoyloxy),
—O—CO—$(CH_2)_4$—CHOH—CH$_2$OH (6,7-dihydroxyheptanoyloxy),
—O—CO—$(CH_2)_5$—OH (6-hydroxyhexanoyloxy),
—O—CO—$(CH_2)_2$—COOH (3-carboxypropanoyloxy)
—O—CO—$(CH_2)_4$—CHO (6-oxohexanoyloxy),
—O—CO—$(CH_2)_5$—NH—CO—$(CH_2)_2$—COOH (3-carboxypropanoylamino hexanoyloxy).

5. A method according to claim 1, wherein $R_1$ and $R_2$ are chosen among:
—CO—CH$_2$—C*H [O—CO—$(CH_2)_{10}$—CH$_3$]—$(CH_2)_{10}$—CH$_3$, (3(C12O)C$_{14}$),
—CO—CH$_2$—C*HOH(CH$_2$)$_{10}$—CH$_3$, (3 (HO)C$_{14}$),
—CO—CH$_3$, (C2),
—CO—CH$_2$—NH—CO—C*H [O—CO—$(CH_2)_8$—CH$_3$]—$(CH_2)_5$—CH$_3$, ([2(C$_{10}$O)C$_8$]NC$_2$),
—CO—C*H[O—CO—$(CH_2)_4$—CH$_3$]—$(CH_2)_5$—CH$_3$, (2(C$_6$O)C8),
—CO—$(CH_2)_{16}$—CH$_3$, (C18), —CO—CH$_2$—C*H[O—CH$_2$—C$_6$H$_5$]—(CH$_2$)$_{10}$—CH$_3$, (3(BnO)C$_{14}$), —CO—CH$_2$—C*H [O—P(O)(OH)$_2$]—(CH$_2$)$_{10}$—CH$_3$, (3 [(OH)$_2$—P(O)O]C$_{14}$), C* corresponding to an asymmetric carbon in configuration R, S, or in the racemic form RS, in the formulae mentioned above.

6. A method according to claim 1, wherein:

R$_1$ is chosen among:
—CO—CH$_2$—C$^{**1}$H [O—CO—(CH$_2$)$_{10}$—CH$_3$]—(CH$_2$)$_{10}$—CH$_3$, (3(C$_{12}$O)C$_{14}$),
—CO—CH$_2$—C$^{**1}$HOH—(CH$_2$)$_{10}$—CH$_3$, (3(HO)C$_{14}$),
—CO—CH$_3$, (C2),
—CO—CH$_2$—NH—CO—C$^{**1}$H[O—CO—(CH$_2$)$_8$]—(CH$_2$)$_5$—CH$_3$, ([2 (C$_{10}$O)C$_8$]NC$_2$),
—CO—C$^{**1}$H [O—CO—(CH$_2$)$_4$—CH$_3$]—(CH$_2$)$_5$—CH$_3$, (2 (C$_6$O)C$_8$),
—CO—(CH$_2$)$_{16}$—CH$_3$, (C18), R$_2$ is chosen among:
—CO—CH$_2$—C$^{**2}$H[O—CO—(CH$_2$)$_{10}$—CH$_3$]—(CH$_2$)$_{10}$—CH$_3$, (3 (C$_{12}$O)C$_{14}$),
—CO—CH$_2$—C$^{**2}$HOH—(CH$_2$)$_{10}$—CH$_3$, (3 (HO)C$_{14}$),
—CO—CH$_2$—C$^{**2}$H[O—CH$_2$—C$_6$H$_5$]—(CH$_2$)$_{10}$—CH$_3$, (3 (BnO)C$_{14}$),
—CO—CH$_2$—C$^{**2}$H[O—P(O)(OH)$_2$]—(CH$_2$)$_{10}$—CH$_3$, (3[(OH)$_2$—P(O)O]C$_{14}$).

C$^{1}$ and C$^{2}$ corresponding to asymmetric carbons in configuration R, S, or in the racemic form RS, in the formulae mentioned above.

7. A method according to claim 1, wherein the administered compound has the general formula (II):

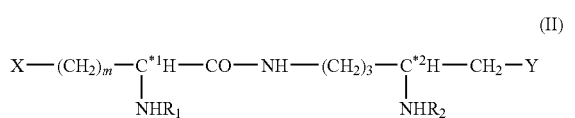

(II)

Wherein X, Y, R$_1$, R$_2$, and m are as defined in anyone of claims 1 to 6, C$^{*1}$ is in configuration R, S, or is the racemic RS, and C$^{*2}$ is in configuration R.

8. A method according to claim 1, wherein the administered compound is selected among those of formula (I) wherein:

X=—O—P(O)(OH)$_2$, Y=—O—P(O)(OH)$_2$, R$_1$=—CO—CH$_2$—C$^{1}$H[O—CO—(CH$_2$)$_{10}$—CH$_3$]—(CH$_2$)$_{10}$—CH$_3$, R$_2$=—CO—CH$_2$—C$^{2}$HOH(CH$_2$)$_{10}$—CH$_3$, m=2, C$^{*1}$ is in configuration S, C$^{*2}$ is in configuration R, C$^{1}$ and C$^{2}$ are in configuration R, i.e. (3S,9R)-3-[(R)-3-dodecanoyloxytetradecanoylamino]-4-oxo-5-aza-9-[(R)-3-hydroxytetradecanoyl amino]-decan-1,10-diol (1,10)-bis-dihydrogenophosphate (OM-294-DP (S,R)), X=—O—P(O)(OH)$_2$, Y=—O—CO—(CH$_2$)$_4$—CHOH—CH$_2$OH, R$_1$=—CO—CH$_2$—C$^{1}$H[O—CO—(CH$_2$)$_{10}$—CH$_3$]—(CH$_2$)$_{10}$—CH$_3$, R$_2$=—CO—CH$_2$—C$^{2}$HOH—(CH$_2$)$_{10}$—CH$_3$, m=2, C$^{*1}$ is in configuration S, and C$^{*2}$ is in configuration R, C$^{1}$ and C$^{2}$ are in configuration R, i.e. (3S, 9R)-3-[(R)-3-dodecanoyloxytetradecanoylamino]-4-oxo-5-aza-9-[(R)-3-hydroxy tetradecanoyl amino]-decan-1, 10-diol 1-dihydrogenophosphate 10(6,7-dihydroxyheptanoate) (OM-197-MP-HD (S,R)), X=—COOH, Y=—O—CO—(CH$_2$)$_4$—CHOH—CH$_2$OH, R$_1$=—CO—CH$_2$—C$^{1}$H[O—CO—(CH$_2$)$_{10}$—CH$_3$]—(CH$_2$)$_{10}$—CH$_3$, R$_2$=—CO—CH$_2$—C$^{2}$HOH—(CH$_2$)$_{10}$—CH$_3$, m=1, C$^{*1}$ is in configuration S, and C$^{*2}$ is in configuration R, C$^{1}$ and C$^{2}$ are in configuration R, i.e. N—[(R)-3-dodecanoyloxytetradecanoyl]-L-aspartic acid, α-N -{(4R)-5-hydroxy-4-[(R)-3-hydroxytetradecanoylamino]pentyl}amide 5-O-(6,7-dihydroxyheptanoate) (OM-197-MC-HD (S,R)), X=—O—P(O)(OH)$_2$, Y=—O—CO—(CH$_2$)$_5$—NH$_2$, R$_1$=—CO—CH$_2$—C$^{1}$H [O—CO—(CH$_2$)$_{10}$—CH$_3$]—(CH$_2$)$_{10}$—CH$_3$, R$_2$=—CO—CH$_2$—C$^{2}$HOH—(CH$_2$)$_{10}$—CH$_3$, m=2, C$^{*1}$ is in configuration S, and C$^{*2}$ is in configuration R, C$^{1}$ and C$^{2}$ are in configuration R, i.e. (3S, 9R)-3-[(R)-3-dodecanoyloxytetradecanoylamino]-4-oxo-5-aza-9-[(R)-3-hydroxytetra decanoylamino]-decan-1, 10-diol 1-dihydrogeno phosphate 10-(6-aminohexanoate) (OM-197-MP-AC (S,R)), X=—NH$_2$, Y=—O—P(O)(OH)$_2$, R$_1$=—CO—CH$_2$—C$^{1}$H[O—CO—(CH$_2$)$_{10}$—CH$_3$]—(CH$_2$)$_{10}$—CH$_3$, R$_2$=—CO—CH$_2$—C$^{2}$HOH—(CH$_2$)$_{10}$—CH$_3$, m=4, C$^{*1}$ is in configuration S, and C$^{*2}$ is in configuration R, C$^{1}$ and C$^{2}$ are in configuration R, i.e. (5S,11R)-1-Amino-5-[(R)-3-dodecanoyloxytetradecanoylamino]-6-oxo-7-aza-11-[(R)-3-hydroxytetra decanoylamino]-dodecan-12-ol 12-dihydrogen phosphate (OM-294-BA-MP (S,R).

9. A method according to claim 1, wherein said disease or disorder is related to an overproduction of inflammatory cytokines by activated T lymphocytes, monocytes, or antigen presenting cells in the organism, wherein the inflammatory cytokines or inflammatory markers belong to the group consisting of IL-4, IL-5 and IL-13.

10. A method according to claim 1 which consists in administering a therapeutically effective amount of said compound in a pharmaceutically-acceptable carrier, excipient or formulation, via a mucosal or parenteral route.

11. A method according to claim 1 which consists in administering a therapeutically effective amount of said compound preferentially via the peritoneal, subcutaneous, oral, intranasal, sublingual, or aerosol routes.

12. A method according to claim 1, wherein the dosages of the immunomodulatory compound range from 0.01 to 50 mg/m$^2$ in humans.

13. A method according to claim 11, wherein

X is selected from the following groups:
carboxyl —COOH,
dihydroxyphosphoryloxy —O—P(O)(OH)$_2$,
hydroxysulfonyloxy —O—SO$_2$(OH),
amino —NH$_2$,
[amino(C$_1$-C$_6$)alkyl]aminocarbonyl —CONH (CH$_2$)$_{n1}$—NH$_2$, with n$_1$ being an integer from 1 to 6,
[dicarboxy(C$_1$-C$_5$)alkyl]aminocarbonyl —CO—NH—CH(COOH)—(CH$_2$)$_{n1}$—COOH, with n$_1$ being an integer from 1 to 5,
{carboxy[amino(C$_1$-C$_5$)alkyl]}aminocarbonyl —CO—NH—CH(COOH)—(CH$_2$)$_{n1}$—NH$_2$ with n$_1$ being an integer from 1 to 5,
amino(C$_2$-C$_{12}$)alkanoyloxy —O—CO—(CH$_2$)$_{n1}$—NH$_2$, with n$_1$ being an integer from 2 to 12, and Y is selected from the following groups:
dihydroxyphosphoryloxy —O—P(O)(OH)$_2$,
hydroxysulfonyloxy —O—SO$_2$ (OH),
amino —NH$_2$,
hydroxyl —OH,
amino(C$_2$-C$_{12}$)alkanoyloxy —O—CO—(CH$_2$)$_{n1}$—NH$_2$, with n$_1$ being an integer from 2 to 12, dihydroxy($C_3$-$C_7$)alkanoyloxy —O—CO—$(CH_2)_{n1}$—CHOH—$CH_2OH$, with $n_1$ being an integer from 3 to 7, hydroxy($C_2$-$C_6$)alkanoyloxy —O—CO—$(CH_2)_{n1}$—OH, with $n_1$ being an integer from 2 to 6, carboxy($C_3$-$C_6$)alkanoyloxy —O—CO—$(CH_2)_{n1}$—COOH, with $n_1$ being an integer from 3 to 6, oxo($C_2$-$C_5$)alkanoyloxy —O—CO—$(CH_2)_{n1}$—CHO, with $n_1$ being an integer from 2 to 5,

[carboxy($C_3$-$C_6$)alkanoyl]amino($C_2$-$C_{12}$)alkanoyloxy —O—CO—$(CH_2)_{n1}$—NH—CO—$(CH_2)_{n2}$—COOH, with $n_1$ being an integer from 3 to 6, and $n_2$ being an integer from 2 to 12.

\* \* \* \* \*